US006797473B2

(12) United States Patent
Korneluk et al.

(10) Patent No.: US 6,797,473 B2
(45) Date of Patent: Sep. 28, 2004

(54) METHODS AND COMPOUNDS FOR MODULATING MALE FERTILITY

(75) Inventors: Robert G. Korneluk, Ottawa (CA); Mark Lagacé, Ottawa (CA)

(73) Assignee: University of Ottawa, Ottawa (CA)

( * ) Notice: Subject to any disclaimer, the term of this patent is extended or adjusted under 35 U.S.C. 154(b) by 141 days.

(21) Appl. No.: 10/024,433

(22) Filed: Dec. 18, 2001

(65) Prior Publication Data

US 2002/0086409 A1 Jul. 4, 2002

Related U.S. Application Data

(63) Continuation of application No. 09/239,867, filed on Jan. 29, 1999, now Pat. No. 6,331,412.
(60) Provisional application No. 60/073,001, filed on Jan. 29, 1998.

(51) Int. Cl.$^7$ .............................. C12N 1/68; C12N 5/00; C12N 15/63; C07H 21/04; C07K 1/00

(52) U.S. Cl. ........................ 435/6; 435/69.1; 435/320.1; 435/325; 435/375; 435/455; 536/23.1; 536/23.5; 530/350

(58) Field of Search ............................ 435/6, 7.1, 69.1, 435/320.1, 325, 375, 455; 536/23.1, 23.5; 530/350

(56) References Cited

U.S. PATENT DOCUMENTS 5,399,346 A    3/1995    Anderson et al. ........ 424/93.21

FOREIGN PATENT DOCUMENTS

| WO | WO 96/01022 | 1/1996 |
| WO | WO 97/00142 | 1/1997 |
| WO | WO 97/00721 | 1/1997 |

OTHER PUBLICATIONS

Deveraux et al, IAP family proteins—suppressors of apoptosis.Genes Dev. 1999 Feb. 1;13(3):239–52.*
Ngo, Computational complexity Protein structure prediction and the Levinthal paradox in The Protein Folding Problem and Tertiary Structure Prediction, Merz et al. (eds.), Birkhauser Boston: Boston, MA, pp. 433 and 492–495, 1994.*
Rudinger Characteristics of amino acids as components of a peptide hormone sequence (in Peptide Hormones, Parsons (ed.), University Park Press: Baltimore, MD, pp. 1–7, 1976).*
Ambrosini et al., "A Novel Anti–Apoptosis Gene, Survivin, Expressed in Cancer and Lymphoma," Nature Medicine 3:917–921 (1997).
Bennett, Biochem Pharmacol. 55:9–19, 1998.
Branch TIBS, Feb. 23, 45–50, 1998.

Birnbaum et al., "An Apoptosis–Inhibiting Gene from a Nuclear Polyhedrosis Virus Encoding a Polypeptide with Cys/His Sequence Motifs," Journal of Virology 68:2521–2528 (1994).
Clem et al., "Anti–Apoptotic Genes of Baculoviruses," Cell Death and Differentiation 3:9–16 (1996).
Clem et al., "Control of Programmed Cell Death by the Baculovirus Genes p35 and iap," Molecular and Cellular Biology 14:5212–5222 (1994).
Clem et al., "Prevention of Apoptosis by a Baculovirus Gene During Infection of Insect Cells," Science 254:1388–1390 (1991).
Crook, Antisense & Nucleic Acid Drug Dev. 8:115–122, 1998.
Crook et al., "An Apoptosis–Inhibiting Baculovirus Gene with a Zinc Finger–Like Motif," Journal of Virology 67:2168–2174 (1993).
Eglitis et al., "Retroviral Vectors for Introduction of Genes into Mammalian Cells," BioTechniques 6:6087–614 (1988).
Evan et al., "Isolation of Monoclonal Antibodies Specific for Human c–myc Proto–Oncogene Product," Molecular and Cellular Biology 5:3610–3616 (1985).
Felgner et al., "Lipofection: A Highly Efficient, Lipid–Mediated DNA–Transfection Procedure," Proc. Natl. Acad. Sci. USA 84:7413–7417 (1987).
Fernandez et al., "Differential Sensitivity of Normal and Ha–Ras–Transformed C3H Mouse Embryo Fibroblasts to Tumor Necrosis Factor: Induction of bcl–2, c–myc, and Manganese Superoxide Dismutase in Resistant Cells," Oncogene 9:2009–2017 (1994).
Fields et al., "A Novel Genetic System to Detect Protein-Protein Interactions," Nature 340:245–246 (1989).
Friedmann, "Progress Toward Human Gene Therapy," Science 244:1275–1281 (1989).
Furuchi et al., "Inhibition of Testicular Germ Cell Apoptosis and Differentiation in Mice Misexpressing Bcl–2 in Spermatogonia," Development 122:1703–1709 (1996).
Goruppi et al., "Dissection of c–myc Domains Involved in S Phase Induction of NIH3T3 Fibroblasts," Oncogene 9:1537–1544 (1994).
Gyuris et al., "Cdi1, a Human G1 and S Phase Protein Phosphatase That Associates with Cdk2," Cell 75:791–803 (1993).
Harrington et al., "c–Myc–induced Apoptosis in Fibroblasts is Inhibited by Specific Cytokines," The EMBO Journal 13:3286–3295 (1994).

(List continued on next page.)

*Primary Examiner*—Jeffrey Fredman
*Assistant Examiner*—Sumesh Kauahal
(74) *Attorney, Agent, or Firm*—Clark & Elbing, LLP; Kristina Bieker-Brady, P.C.

(57) ABSTRACT

The invention features methods and reagents useful for the treatment of excessive or insufficient apoptosis in cells, and, particularly, in germ-line cells. The invention is useful in treating testicular cancers, cancers of germ-line cells, cancers in non-germ-line cell tissues, infertility (e.g., male infertility), and for birth control (e.g., male birth control).

4 Claims, 8 Drawing Sheets

OTHER PUBLICATIONS

Hogervorst et al., "Rapid Detection of BRCA1 Mutations by the Protein Truncation Test," Nature Genetics 10:208–212 (1995).

Hsueh et al., "Gonadal Cell Apoptosis," Recent Progress In Hormone Research 51:433–456 (1996).

Itoh et al., "A Novel Protein Domain Required for Apoptosis; Mutational Analysis of Human Fas Antigen," The Journal of Biological Chemistry 268:10932–10937 (1993).

Kobayshi et al., "Expression of a Murine Homologue of the Inhibitor of Apoptosis Protein is Related to Cell Proliferation," Proc. Natl. Acad. Sci. USA 96:1457–1462 (1999).

Kohler et al., "Derivation of Specific Antibody–Producing Tissue Culture and Tumor Lines by Cell Fusion," European Journal of Immunology 6:511–519 (1976).

Kohler et al., "Continuous Cultures of Fused Cells Sereting Antibody of Predefined Specificity," Nature 256:495–497 (1975).

LaCasse et al., "The Inhibitors of Apoptosis (IAPs) and Their Emerging Role in Cancer," Oncogene 17:3247–3259 (1998).

Liston et al., "Suppression of Apoptosis in Mammalian Cells by NAIP and a Related Family of IAP Genes," Nature 379:349–353 (1996).

Miller, "Retrovirus Packaging Cells," Human Gene Therapy 1:5–14 (1990).

Orita et al., "Detection of Polymorphisms of Human DNA by Gel Electrophoresis as Single–Strand Conformation Polymorphisms," Proc. Natl. Acad. Sci. USA 86:2766–2770 (1989).

Rabizadeh et al., "Expression of the Baculovirus p35 Gene Inhibits Mammalian Neural Cell Death," Journal of Neurochemistry 61:2318–2321 (1993).

Rosenberg et al., "Gene Transfer into Humans–Immunotherapy of Patients with Advanced Melanoma, Using Tumor–Infiltrating Lymphocytes Modified by Retroviral Gene Transduction," The New England Journal of Medicine 323:370–378 (1990).

Roy et al., "The Gene for Neuronal Apoptosis Inhibitory Protein is Partially Deleted in Individuals with Spinal Muscular Atrophy," Cell 80:167–178 (1995).

Sheffield et al., "Attachment of a 40–Base–Pair G+C–Rich Sequence (GC–Clamp) to Genomic DNA Fragments by the Polymerase Chain Reaction Results in Improved Detection of Single–Base Changes," Proc. Natl. Acad. Sci. USA 86:232–236 (1989).

Smith et al., "Single–Step Purification of Polypeptides Expressed in *Escherichia coli* as Fusions with Glutathione S–Transferase," Gene 67:31–40 (1988).

Vossbeck et al., "Direct Transforming Activity of TGF–$\beta$ on Rat Fibroblasts," International Journal of Cancer 61:92–97 (1995).

Wolff et al., "Direct Gene Transfer into Mouse Muscle in Vivo," Science 247:1465–1468 (1990).

Wu et al., "Receptor–Mediated Gene Delivery and Expression in Vivo," The Journal of Biological Chemistry 263:14621–14624 (1988).

Yap et al., "Slide PCR: DNA Amplification from Cell Samples on Microscopic Glass Slides," Nucleic Acids Research 19:4294 (1991).

* cited by examiner

FIG. 3
XIAP
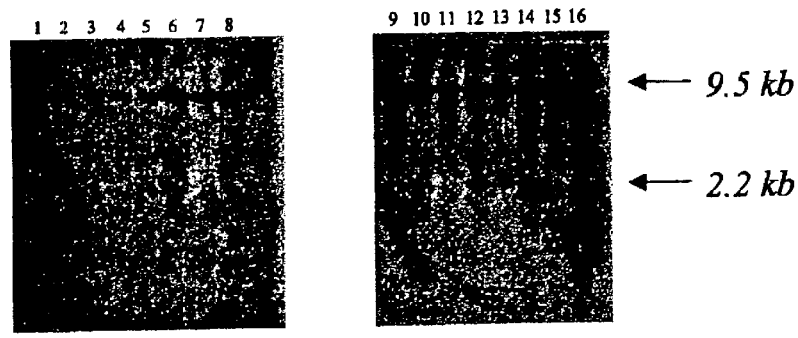
Actin control
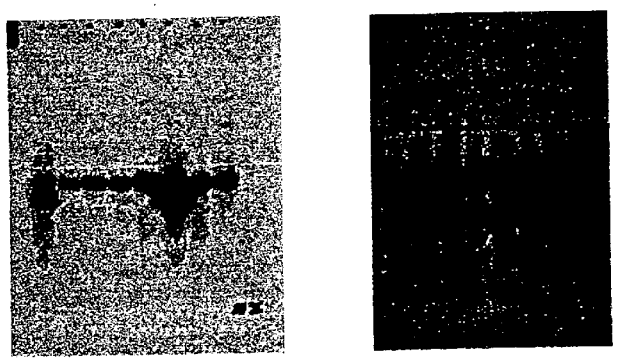
1. Heart
2. Brain
3. Placenta
4. Lung
5. Liver
6. Smooth muscle
7. Kidney
8. Pancreas
9. Spleen
10. Thymus
11. Prostate
12. Testis
13. Ovary
14. Small intestine
15. Colon
16. Peripheral blood leukocyte

```
  1 MTGYEARLITFGTWMYSVNKEQLARAGFYAIGQEDKVQCFHQGGGLANWK  50
    |.:|||||::|||||:||||||||||||||||:|:::|||.||||||||.:||
273 MADYEARIFTFGTWIYSVNKEQLARAGFYALGEGDKVKCFHQGGGLTDWK 322

51 PKEDPWEQHAKWYPGCKYLLEEKGHEYINNIHLTRSLEGALVQTTKKTPS 100
    |.|||||||||||||||||||:||:|||||||||:|||:.||.||.||||
323 PSEDPWEQHAKWYPGCKYLLEQKGQEYINNIHLTHSLEECLVRTTEKTPS 372

101 LTKRISDTIFPNPMLQEAIRMGFDFKDVKKIMEERIQTSGSNYKTLEVLV 150
    ||:||.||||.|||:|||||||.|||:|||||||:|.||||||.|||||
373 LTRRIDDTIFQNPMVQEAIRMGFSFKDIKKIMEEKIQISGSNYKSLEVLV 422

151 ADLVSAQKDTTENELNQTSLQREISPEEPLRRLQEEKLCKICMDRYIAVV 200
    ||||.||||. ::| .|||||:|||.||.||||||||||||||||| ||:|
423 ADLVNAQKDSMQDESSQTSLQKEISTEEQLRRLQEEKLCKICMDRNIAIV 472

201 FIPCGHLVTCKQAEAVDRCPMCSAVIDFKQRVFMS 236
    |:|||||||||||||||||||:||||.||.|||::|||
473 FVPCGHLVTCKQAEAVDKCPMCYTVITFKQKIFMS 508
```

FIG. 6

5' UTR of TIAP cDNA

```
  1 CAACTACACACGTGTGTGTGCGCGTGTGTATAAAACACAGTGCACTAATA  50
 51 CTCAGCCTTTAAAAAAAATGCCACTTGCAACAACGTAGATGGAGCTGGAC 100
101 GATATCATGCTAAAATTATGCAAAGTGAAACAAGCACAAAAAAGAACGAG 150
151 ACACGGGCGTGGGGCACGAGGTGCTCACTGXGCAAGCGCCCACTCCACCG 200
201 CGTGGTTTCCAGCTGGAGGCTGGGAGCGTTXGTGGCTTCCTCTTTTCTTG 250
251 CTGACCCTTCGGAG CTCTGGGAAGTGGCTGCACCTTGGCGGCTCCCCAGA 300
301 GCGCGCGGTGCTAATCGTGGGTCGTCAGCCTGGGTGGCTGGGCCCGGCTT 350
351 AGGGCAGGGTTTGGCATTTCCAATGGTAGGGGCTCGGACCGTCCCTCCG  400
401 CGGGACCCTCCCGTTGGGACAAGGCCGATCGCCTGGGCGGTTGGAGCCGC 450
451 TATCCTGGCGCGAGACGG TGGACAAGTCCTATATTCAAGAAG ATA CT   500
```

5'UTR probe            Equivalent position of XIAP start codon

US 6,797,473 B2

METHODS AND COMPOUNDS FOR MODULATING MALE FERTILITY

CROSS REFERENCE TO RELATED APPLICATIONS

This application is a continuation of U.S. Utility application Ser. No. 09/239,867, filed Jan. 29, 1999 now U.S. Pat. No. 6,331,412, which claims benefit from U.S. Provisional Application Serial No. 60/073,001, filed Jan. 29, 1998 (now abandoned).

BACKGROUND OF THE INVENTION

The invention relates to apoptosis in cells, particularly cell involved in fertility.

Apoptosis is a fundamental process of cell death required for the elimination of unwanted cells in multicellular organisms and involves an ordered cascade of events leading to hallmark morphological changes including nuclear condensation, chromosome laddering, and membrane blebbing. In one specific example, apoptosis plays a prominent role during all stages of sperm development. Spermatogenesis is a process that results in the generation of mature sperm cells from primary germ cells, and some of the events affected by apoptosis include the elimination of unwanted cells and the prevention of the death of those cells destined to become functional sperm (Hsueh et al., Recent Prog. Horm. Res. 51: 433, 1996; Furuchi et al., Development 122: 1703, 1996).

Much of the current knowledge of the biochemical pathways involved in apoptosis comes from the study of viruses. The baculoviral proteins involved in apoptosis, CpIAP and OpIAP, are characterized by two amino terminal cys/his motifs ($Xaa_3$—R—$Xaa_{20\text{-}23}$—G—$Xaa_{11}$—C—$Xaa_2$—C—$Xaa_{16}$—H—$Xaa_6$—C—$Xaa_3$) (SEQ ID NOs: 6–9) and a carboxy terminal C—$Xaa_2$—C—$Xaa_{11}$—C—Xaa—H—$Xaa_3$—C—$Xaa_2$—C—$Xaa_{6-C-Xaa2}$—C RING zinc finger motif (SEQ ID NO: 10) reviewed in Clem et al., Cell Death Differ. 3: 9, 1996). The two amino terminal motifs, termed Baculovirus IAP Repeat (BIR) domains, are the hallmark of the IAP family of proteins and are present as two or three copies in all IAP members discovered to date.

The first mammalian IAP (inhibitor of apoptosis protein), NAIP, was identified during a positional cloning effort seeking candidate genes for spinal muscular atrophy (Roy et al., Cell 80: 167, 1995). Following the identification of NAIP, three other human IAPs, HIAP-1, HIAP-2, and XIAP (Liston et al., Nature 379: 349, 1996), and their murine homologues MIAP-1, MIAP-2, and MIAP-3 (Farahani et al., Genomics 42: 514, 1997), have been reported. In addition, two Drosophila IAPs, DIAP-1 and DIAP-2, and one chicken IAP, ITA have been described (see Liston et al., Apoptosis 2: 423, 1997). A structural comparison of these IAPs is shown in FIG. 1.

The physiological role of XIAP remains elusive. Recent work has demonstrated that XIAP directly inhibits two of the caspases, namely caspase-3 (also known as CPP32, Apopain, or YAMA) and caspase-7 (Devereaux et al., Nature 388: 300, 1997).

SUMMARY OF THE INVENTION

In general, the invention features methods and reagents useful for the treatment of excessive or insufficient apoptosis, particularly in testicular cells. The methods and reagents of the invention are useful in diagnosing and treating testicular cancers, cancers in non-testicular tissues, male infertility, and for achieving male birth control.

In a first aspect, the invention features a substantially pure nucleic acid molecule encoding a TIAP polypeptide. In one embodiment, the nucleic acid molecule has a sequence that is substantially identical to SEQ ID NO: 1. In another embodiment, the nucleic acid molecule has a sequence that hybridizes under high stringency conditions to SEQ ID NO: 1. In other embodiments, the TIAP polypeptide has a sequence that is substantially identical to SEQ ID NO: 2, or has a sequence that is at least 80% identical to SEQ ID NO: 2. In a preferred embodiment, the TIAP has the amino acid sequence of SEQ ID NO.: 2 or the nucleic acid sequence of SEQ ID NO.: 1. Preferably, identity is measured using sequence software analysis, such as the Sequence Analysis Software Package of the Genetics Computer Group. TIAP polypeptides encoded by the aforementioned nucleic acids are another aspect of the invention.

In a second aspect, the invention features a substantially pure nucleic acid molecule corresponding to at least fifteen nucleotides of a nucleic acid molecule encoding a TIAP polypeptide, where the nucleic acid molecule is an antisense nucleic acid molecule that is sufficient to decrease TIAP biological activity. In various embodiments, the antisense nucleic acid molecule corresponds to: at least thirty nucleotides of a nucleic acid molecule encoding a TIAP polypeptide, at least fifty nucleotides of a nucleic acid molecule encoding a TIAP polypeptide, or at least 100 nucleotides of a nucleic acid molecule encoding a TIAP polypeptide. In other preferred embodiments, the TIAP biological activity is decreased by at least 20%, at least 40%, at least 60%, or at least 80%. In yet another embodiment of the second aspect of the invention, the antisense nucleic acid molecule is in a vector that is capable of directing expression of the antisense nucleic acid molecule in a vector-containing cell.

In a third aspect, the invention features a vector including a substantially pure nucleic acid molecule encoding a TIAP polypeptide, the vector being capable of directing expression of the polypeptide in a vector-containing cell.

In a fourth aspect, the invention features a cell that contains a substantially pure nucleic acid molecule encoding a TIAP polypeptide. In one preferred embodiment, the nucleic acid molecule is expressed in the cell. In another embodiment, the cell is selected from a cell from the testis. In yet another embodiment, the cell is present in an animal having a condition that is associated with excessive or insufficient cell death.

In a fifth aspect, the invention features a transgenic animal generated from a cell genetically engineered to lack a nucleic acid molecule encoding a TIAP polypeptide, where the transgenic animal lacks expression of the TIAP polypeptide.

In a sixth aspect, the invention features a transgenic animal generated from a cell that contains a substantially pure nucleic acid molecule replacing DNA encoding a TIAP polypeptide, where the nucleic acid molecule is expressed in the transgenic animal.

In one embodiment of the first six aspects of the invention, the nucleic acid molecule is from an animal. In another embodiment, the nucleic acid molecule is genomic DNA or cDNA. In a preferred embodiment of the first six aspects of the invention, the nucleic acid molecule is operably linked to regulatory sequences for expression of the polypeptide and where the regulatory sequences include a promoter. Such a promoter may be from the TIAP gene, or may be selected from the group consisting of a constitutive promoter, a promoter that is inducible by one or more external agents, and a cell-type specific promoter.

In a seventh aspect, the invention features a method of identifying a compound that modulates TIAP biological activity that includes: (a) providing a cell including a TIAP gene; (b) contacting the cell with a candidate compound; and (c) measuring expression of the TIAP gene, where an alteration in the expression in response to the candidate compound relative to an cell not contacted with the candidate compound indicates a compound that modulates TIAP biological activity. In one embodiment of this aspect of the invention, the cell is transformed.

In an eighth aspect, the invention features a method of identifying a compound that modulates TIAP biological activity that includes: (a) providing a cell including a reporter gene operably linked to a promoter from a TIAP gene; (b) contacting the cell with a candidate compound; and (c) measuring expression of the reporter gene, where an alteration in the expression in response to the candidate compound relative to an cell not contacted with the candidate compound indicates a compound that modulates TIAP biological activity. In one embodiment of this aspect of the invention, the cell is transformed.

In a ninth aspect, the invention features a method of identifying a compound that is able to modulate TIAP biological activity in a cell that includes the steps of: (a) providing a expressing a normal amount of TIAP; (b) contacting the cell with a candidate compound; and (c) measuring level of apoptosis in the cell, where an alteration in the level relative to a level in a cell not contacted with the candidate compound indicates a compound that modulates TIAP biological activity. Preferably, the cell is a germ-line cell.

In one embodiment of the seventh, eighth, and ninth aspect of the invention, the alteration that is an increase indicates the compound is inhibiting TIAP biological activity, and the alteration that is a decrease indicates the compound is increasing TIAP biological activity. In other embodiments, the TIAP is from an animal.

In a tenth aspect, the invention features a method of increasing apoptosis in a cell that includes administering to the cell an apoptosis-inducing amount of a TIAP polypeptide or fragment thereof. Preferably, the cell is a germ-line cell.

In an eleventh aspect, the invention features a method of increasing apoptosis in a cell, the method including administering to the cell a compound which modulates TIAP biological activity. Such a compound may be selected from a group consisting of a neutralizing antibody that specifically binds to TIAP, a polypeptide fragment of a TIAP polypeptide, a mutant of a TIAP polypeptide, a TIAP antisense nucleic acid molecule, and a nucleic acid molecule encoding a TIAP polypeptide, a mutant thereof, or a polypeptide fragment thereof. Preferably, the cell is a germ-line cell.

In one embodiment of the tenth and eleventh aspects of the invention, the cell is in an animal. In another embodiment, the TIAP is from an animal. In preferred embodiments, the animal is desired to have reduced fertility, is diagnosed with cancer, or has a predisposition to develop cancer, for example, a cancer that is selected from a group consisting of testicular cancer, scrotal cancer, prostate cancer, and a cancer in which aberrant expression of TIAP is observed.

In a twelfth aspect, the invention features a method of increasing fertility in an animal that includes providing a transgene encoding a TIAP polypeptide or fragment thereof to a cell of the animal, the transgene being positioned for expression in the cell. Preferably, the cell is a germ-line cell.

In a thirteenth aspect, the invention features a method of increasing fertility in an animal that includes administering to a cell of the animal an excessive amount of TIAP polypeptide or fragment thereof. Preferably, the cell is a germ-line cell.

In a fourteenth aspect, the invention features a method of increasing fertility in an animal that includes administering to a cell of the animal a compound which modulates TIAP biological activity. Preferably, the cell is a germ-line cell. Such a compound may be selected from the group consisting of a full-length TIAP polypeptide, a fragment of a TIAP polypeptide, and a nucleic acid molecule encoding a TIAP polypeptide.

In various embodiments of the twelfth, thirteenth, and fourteenth aspects of the invention, the animal is diagnosed as having a condition involving excessive apoptosis, for example, a condition that is associated with reduced fertility.

In a fifteenth aspect, the invention features a method of diagnosing an animal for the presence of disease involving altered apoptosis or an increased likelihood of developing a disease involving altered apoptosis. Preferably the apoptosis is in a germ-line cell. The method includes isolating a sample of a nucleic acid molecule from the animal and determining whether the nucleic acid molecule includes a TIAP mutation, the mutation being an indication that the animal has an apoptosis disease or an increased likelihood of developing a disease involving apoptosis in a cell (e.g., a germ-line cell).

In a sixteenth aspect, the invention features a second method of diagnosing an animal for the presence of a disease involving altered apoptosis or an increased likelihood of developing a disease involving altered apoptosis. Preferably the apoptosis is in a germ-line cell. The second method includes measuring TIAP gene expression in a sample from the animal, an alteration in the expression relative to a sample from an unaffected animal being an indication that the animal has an apoptosis disease or increased likelihood of developing an apoptosis disease in a cell (e.g., a germ-line cell). In a preferred embodiment of this aspect of the invention, the gene expression is measured by assaying the amount of TIAP polypeptide or TIAP biological activity in the sample. In another embodiment of this aspect of the invention, the TIAP polypeptide is measured by immunological methods or by assaying the amount of TIAP RNA in the sample.

In a seventeenth aspect, the invention features a kit for diagnosing an animal for the presence of a disease involving altered apoptosis or an increased likelihood of developing a disease involving altered apoptosis, where the kit includes a substantially pure antibody that specifically binds a TIAP polypeptide.

In an eighteenth aspect, the invention features kit for diagnosing an animal for the presence of a disease involving altered apoptosis or an increased likelihood of developing a disease involving altered apoptosis, where the kit includes a material for measuring TIAP RNA.

In a nineteenth aspect, the invention features a kit for diagnosing an animal for the presence of a disease involving altered apoptosis or an increased likelihood of developing a disease involving altered apoptosis, where the kit includes: (a) a substantially pure antibody that specifically binds a TIAP polypeptide; or (b) a material for measuring TIAP RNA. Preferably, the kit has both the antibody and the material for measuring TIAP RNA. In a preferred embodiment of this aspect of the invention, the kit further includes a means for detecting the binding of the antibody to the TIAP polypeptide. In another embodiment, the material for measuring TIAP RNA is a nucleic acid probe.

In a twentieth aspect, the invention features a method of obtaining a TIAP polypeptide that includes: (a) providing a cell with a nucleic acid molecule encoding a TIAP polypeptide, the nucleic acid molecule being positioned for expression in the cell; (b) culturing the cell under conditions for expressing the nucleic acid molecule; and (c) isolating the TIAP polypeptide. In one embodiment of this aspect of the invention, the nucleic acid molecule further includes a promoter that is inducible by one or more external agents.

In a twenty-first aspect, the invention features a method of isolating a TIAP gene or portion thereof having sequence identity to human TIAP that includes amplifying by polymerase chain reaction the TIAP gene or portion thereof using oligonucleotide primers where the primers: (a) are each greater than 13 nucleotides in length; (b) each have regions of complementarity to opposite DNA strands in a region of the nucleotide sequence of SEQ ID NO: 1; and (c) optionally contain sequences capable of producing restriction endonuclease cut sites in the amplified product; and isolating the TIAP gene or portion thereof.

In a twenty-second aspect, the invention features a method of isolating a TIAP gene or fragment thereof from a cell that includes: (a) providing a sample of cellular nucleic acid; (b) providing a pair of oligonucleotides having sequence identity to a conserved region of a TIAP gene; (c) combining the pair of oligonucleotides with the cellular nucleic acid sample under conditions suitable for polymerase chain reaction-mediated nucleic acid amplification; and (d) isolating the amplified TIAP gene or fragment thereof.

In a preferred embodiment of the twentieth, twenty-first, and twenty-second aspects of the invention, the polymerase chain reaction is carried out using a reverse-transcription polymerase chain reaction. In another embodiment, the reverse-transcription polymerase chain reaction is RACE.

In a twenty-third aspect, the invention features a method of identifying a TIAP gene in a cell from an animal that includes: (a) providing a sample of cellular nucleic acid from the animal; (b) providing a detectably-labeled nucleic acid sequence having identity to a conserved region of a known TIAP gene; (c) contacting the sample with the detectably-labeled nucleic acid sequence under hybridization conditions that provide detection of genes having 50% or greater nucleotide sequence identity to the detectably labeled nucleic acid sequence; and (d) identifying the TIAP gene. Preferably, the nucleic acid sequence includes at least a portion of SEQ ID NO: 1.

In a twenty-fourth aspect, the invention features a method of identifying a TIAP gene that includes: (a) providing a cell sample from an animal; (b) introducing by transformation into the cell sample a candidate TIAP gene; (c) expressing the candidate TIAP gene within the cell sample; and (d) determining whether the sample exhibits an altered level of apoptosis whereby an alteration in the level of apoptosis identifies a TIAP gene. In one embodiment of this aspect of the invention, the cell sample is selected from the group consisting of a spermatogonium, a spermatocyte, a spermatid, a sperm cell, a Sertoli cell, a fibroblast, a neuron, a myocardial cell, and an embryonic stem cell.

In a twenty-fifth aspect, the invention features a TIAP polypeptide. The polypeptide may be used in modulating apoptosis in a cell. Preferably, the cell is a germ-line cell.

In a twenty-sixth aspect, the invention features a substantially pure antibody that specifically binds a TIAP polypeptide, or a fragment or a mutant thereof. In one embodiment of this aspect of the invention, the TIAP polypeptide is from an animal.

In twenty-seventh aspect, the invention features a substantially pure nucleic acid molecule operably linked to a nucleic acid sequence encoding a TIAP polypeptide. In one embodiment, nucleic acid molecule is a TIAP gene promoter. In another embodiment, the nucleic acid molecule has a nucleic acid sequence that is substantially identical to a sequence found within SEQ ID NO: 5.

In a twenty-eighth aspect, the invention features a transgenic animal generated from a cell that contains a substantially pure nucleic acid molecule operably linked to a TIAP gene promoter. In one embodiment of this aspect of the invention, the TIAP gene promoter has a nucleic acid sequence that is substantially identical to a sequence found within SEQ ID NO: 5. In another embodiment, the nucleic acid molecule encodes a toxin, for example, diptheria toxin or ricin.

By "TIAP" is meant a protein or polypeptide which is a member of the IAP family of proteins and which is encoded by a nucleic acid molecule having a high degree of sequence identity to the upper nucleic acid sequence shown in FIG. 4A (SEQ ID NO: 1). Preferably, the sequence encoding TIAP is at least 80%, preferably at least 85%, more preferably at least 90%, and most preferably at least 95% identical to SEQ ID NO: 1. Preferably, identity is measured using sequence software analysis, such as the Sequence Analysis Software Package of the Genetics Computer Group.

By "germ-line cell" is meant a cell, progenitor, or progeny thereof, which is a product of a meiotic cell division. Preferably, the germ-line cell of the invention is a male germ-line cell and resides in the testis.

By "male birth control" is meant a composition which, when administered to a male animal, reduces the sperm count in the administered animal relative to the same animal not administered the male birth control composition. Preferably, the reduction in sperm count is at least 10%, preferably 20%, more preferably at least 50%, and most preferably, at least 80%, as compared to an animal not administered the male birth control.

By "BIR domain" is meant a domain having the amino acid sequence of the consensus sequence: $Xaa_3$—Arg—$Xaa_{20-23}$—Gly—$Xaa_{11}$—Cys—$Xaa_2$—Cys—$Xaa_{16}$—His—$Xaa_6$—Cys—$Xaa_3$, wherein Xaa is any amino acid residue (SEQ ID NOs: 6–9). Preferably, the sequence is substantially identical to one of the BIR domain sequences provided for XIAP or TIAP described herein.

By "ring zinc finger" or "RZF" is meant a domain having the amino acid sequence of the consensus sequence: C—$Xaa_2$—C—$Xaa_{11}$—C—Xaa—H—$Xaa_3$—C—$Xaa_2$—C—$Xaa_6$—C—$Xaa_2$—C, where Xaa is any amino acid (SEQ ID NO: 10). Preferably, the sequence is substantially identical to the RZF domains provided herein for XIAP or TIAP.

By "modulating apoptosis" or "altering apoptosis" is meant increasing or decreasing the number of cells which undergo apoptosis in a given cell population. Preferably, the cell population is selected from a group including spermatogonium, spermatocytes, epithelial cells, fibroblasts, or any other cell line known to undergo apoptosis in a laboratory setting (e.g., the baculovirus infected insect cells). It will be appreciated that the degree of modulation provided by a TIAP or modulating compound in a given assay will vary, but that one skilled in the art can determine the statistically significant change in the level of apoptosis which identifies a TIAP or a compound which modulates a TIAP.

By "inhibiting apoptosis" is meant any decrease in the number of cells which undergo apoptosis relative to an untreated control. Preferably, the decrease is at least 25%, more preferably the decrease is 50%, and most preferably the decrease is at least one-fold.

By "polypeptide" is meant any chain of amino acids, regardless of length or post-translational modification (e.g., glycosylation or phosphorylation).

By "substantially identical" is meant a polypeptide or nucleic acid exhibiting at least 50%, preferably 85%, more preferably 90%, and most preferably 95% identity to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By a "substantially pure polypeptide" is meant a polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, polypeptide. A substantially pure TIAP polypeptide may be obtained, for example, by extraction from a natural source (e.g., testis); by expression of a recombinant nucleic acid encoding a TIAP polypeptide; or by chemically synthesizing the protein. Purity can be measured by any appropriate method, e.g., column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

By "substantially pure nucleic acid molecule" is meant nucleic acid molecule that is free of the genes which, in the naturally-occurring genome of the organism from which the nucleic acid molecule of the invention is derived, flank the gene. The term therefore includes, for example, a recombinant nucleic acid molecule which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR amplification or restriction endonuclease digestion) independent of other sequences. It also includes a recombinant DNA which is part of a hybrid gene encoding additional polypeptide sequence.

By "purified antibody" is meant antibody which is at least 60%, by weight, free from proteins and naturally-occurring organic molecules with which it is naturally associated. Preferably, the preparation is at least 75%, more preferably 90%, and most preferably at least 99%, by weight, antibody, e.g., a TIAP-specific antibody. A purified antibody may be obtained, for example, by affinity chromatography using recombinantly-produced protein or conserved motif peptides and standard techniques.

By "specifically binds" is meant an antibody which recognizes and binds a protein but which does not substantially recognize and bind other molecules in a sample, e.g., a biological sample, which naturally includes protein.

By "toxin" is meant a protein or polypeptide which kills the cell in which it is expressed. Exemplary toxins include, without limitation, diptheria toxin, cholera toxin, and ricin.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic mammals (e.g., rodents, such as rats or mice) and the DNA (transgene) is inserted by artifice into the nuclear genome.

By "transformation" is meant any method for introducing foreign molecules into a cell. Lipofection, calcium phosphate precipitation, retroviral delivery, electroporation and biolistic transformation are just a few of the teachings which may be used. For example, biolistic transformation is a method for introducing foreign molecules into a cell using velocity driven microprojectiles such as tungsten or gold particles. Such velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles (e.g., mitochondria and chloroplasts), bacteria, yeast, fungi, algae, animal tissue, and cultured cells.

By "transformed cell" is meant a cell into which (or into an ancestor of which) has been introduced, by means of recombinant DNA techniques, a DNA molecule encoding (as used herein) a TIAP polypeptide.

By "positioned for expression" is meant that the DNA molecule is positioned adjacent to a DNA sequence which directs transcription and translation of the sequence (i.e., facilitates the production of, e.g., a TIAP polypeptide, a recombinant protein or a RNA molecule).

By "high stringency conditions" is meant hybridization in 2× SSC at 40° C. with a nucleic acid probe length of at least 30 nucleotides. For other definitions of high stringency conditions, see Ausubel et al., 1994, *Current Protocols in Molecular Biology*, John Wiley & Sons, New York, 6.3.1–6.3.6, hereby incorporated by reference.

By "reporter gene" is meant a gene whose expression may be assayed; such genes include, without limitation, β-glucuronidase (GUS), luciferase, chloramphenicol transacetylase (CAT), and β-galactosidase.

By "promoter" is meant minimal sequence sufficient to direct transcription. Also included in the invention are those promoter elements which are sufficient to render promoter-dependent gene expression controllable for cell-type specific, tissue-specific or inducible by external signals or agents; such elements may be located in the 5' or 3' regions of the native gene.

By "operably linked" is meant that a gene and a regulatory sequence(s) are connected in such a way as to permit gene expression when the appropriate molecules (e.g., transcriptional activator proteins) are bound to the regulatory sequence(s).

By "detectably-labelled" is meant any means for marking and identifying the presence of a molecule, e.g., an oligonucleotide probe or primer, a gene or fragment thereof, or a cDNA molecule. Methods for detectably-labelling a molecule are well known in the art and include, without limitation, radioactive labelling (e.g., with an isotope such as $^{32}P$ or $^{35}S$) and nonradioactive labelling (e.g., chemiluminescent labelling, e.g., fluorescein labelling).

By "antisense," as used herein in reference to nucleic acids, is meant a nucleic acid sequence that is complementary to the coding strand of a gene, preferably, a TIAP gene. The preferred antisense nucleic acid molecule is one which is capable of lowering the level of polypeptide encoded by the complementary gene when both are expressed in a cell. Preferably, the polypeptide level is lowered by at least 10%, more preferably at least 25%, and most preferably, at least 50%, as compared to the polypeptide level in a cell expressing only the gene, and not the complementary antisense nucleic acid molecule.

BRIEF DESCRIPTION OF THE DRAWINGS

FIG. 3 is a series of Northern blots showing polyadenylated RNA from various tissues probed with a full length XIAP coding region probe (top two blots), and probed with an actin control (lower two blots). The RNA of tissues probed are in the lanes as follows: 1, heart; 2, brain; 3, placenta; 4, lung; 5, liver; 6, smooth muscle; 7, kidney; 8, pancreas; 9, spleen; 10, thymus; 11, prostate; 12, testis; 13, ovary; 14, small intestine; 15, colon; 16, peripheral blood leukocyte. A ubiquitous 9.5 kb band appears in all tissues tested (except peripheral blood leukocytes). A second, smaller transcript (2.2 kb) is present only in the testis lane.

FIG. 4A shows the nucleotide sequence alignment between TIAP (upper sequence; SEQ ID NO: 1) and XIAP (lower sequence; SEQ ID NO: 3). Dots ( . . . ) represent gaps introduced into a sequence for alignment purposes. Pairwise alignment was performed using the "bestfit" program of GCG. Total percent identity over the region shown is 84.3%. The START (ATG) and STOP (TAA) codons from each sequence are boxed and indicated.

FIG. 4B shows the amino acid sequence alignment between the first 236 residues of TIAP (upper sequence; SEQ ID NO: 2) and residues 273–508 from XIAP (lower sequence; SEQ ID NO: 4). Critical residues in the BIR domain and the ring zinc finger are boxed. Pairwise comparison was performed using the bestfit program of GCG. Percent identity over the entire region shown is 80.1%. Percent similarity is 90.3%. Note that the conservation of critical (i.e., boxed) amino acids is perfect.

FIG. 6 shows nucleotide sequence from the partial 5' untranslated region (5' UTR) of TIAP cDNA (SEQ ID NO: 5). The boxed sequence labelled "5' UTR probe" is the sequence of the TIAP specific probe used in FIGS. 7A and 7B. The relative position of the start codon in XIAP is also shown.

DETAILED DESCRIPTION

Figure 1:
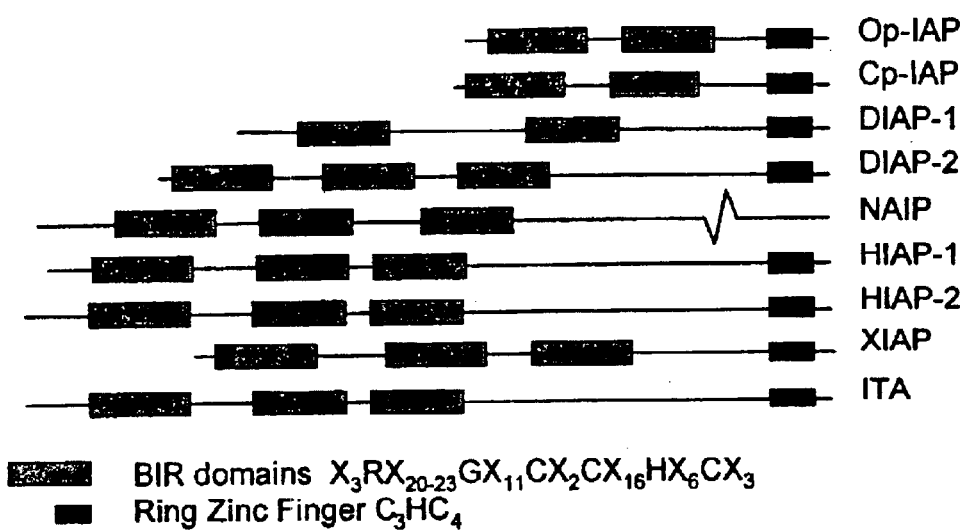
FIG. 1 is a schematic diagram showing a structural comparison between members of the IAP family, where the larger gray boxes represent the BIR domains and the smaller black boxes represent the ring zinc finger domain.

Since the mammalian IAP protein, XIAP, is X-linked, we hypothesized that a homologue of this protein was likely to be found in cells lacking a functional X chromosome. We describe herein our discovery of TIAP, the Testes-specific XIAP homologue.

I. TIAP, the Testes-specific XIAP Homologue

We have discovered TIAP, a new member of the IAP family of proteins that is expressed in the testis. TIAP proteins may be used to modulate apoptosis. For example, TIAP polypeptides or nucleic acid molecules encoding TIAP polypeptides may be administered for the treatment of or prevention of apoptosis which occurs as a part of testicular cancer and male infertility. TIAP may be manipulated for use as a male birth control.

II. Detection of TIAP Gene Expression

Antibodies which specifically bind to TIAP polypeptides may be used to monitor TIAP protein expression. In addition, in situ hybridization is a method which may be used to detect the expression of TIAP genes. In situ hybridization techniques, such as fluorescent in situ hybridization (FISH), rely upon the hybridization of a specifically labelled nucleic acid probe to the cellular RNA in individual cells or tissues. Therefore, it allows the identification of mRNA within intact tissues, such as the testis. In this method, oligonucleotides or cloned nucleotide (RNA or DNA) fragments corresponding to unique portions of TIAP genes are used to detect specific mRNA species, e.g., in the heart. Numerous other gene expression detection techniques are known to those of skill in the art and may be employed here.

Since TIAP is normally expressed in testicular tissues, an inappropriate expression of TIAP in non-testicular tissues may indicate a condition involving abnormally low levels of apoptosis, which may indicate a cancerous condition, or identify an individual predisposed to develop cancer, particularly a cancer of the tissue in which TIAP is inappropriately expressed. Such an individual may be treated with antisense TIAP nucleic acid molecules or TIAP-specific antibodies, especially such reagents targeted toward the affected tissues, using the techniques and reagents described below.

Alternatively, abnormal expression of TIAP in non-germline tissue may indicate a reduced level of expression of XIAP, or another apoptosis-inhibiting protein in that tissue. Such an individual may be tested for expression of XIAP or other apoptosis-inhibiting proteins (e.g., NAIP, HIAP-1, or HIAP-2) using a variety of methods and reagents, including those described in U.S. Ser. No. 08/511, 485 (now U.S. Pat. No. 5,919,912), Ser. No. 08/576,956 (now U.S. Pat. No. 6,156,535), Ser. No. 60/017,354 (now abandoned), Ser. No. 60/030,590 (now abandoned), Ser. No. 08/844,693 (now U.S. Pat. No. 6,159,948), Ser. No. 08/913, 322 (now U.S. Pat. No. 20,020,137,028), and Ser. No. 08/180,929 (now U.S, Pat. No. 6,133,437), and PCT applications PCT/1B97/00721, PCT/1B97/00142, and PCTSB96/01022, hereby incorporated by reference.

III. TIAP Protein Expression

TIAP genes may be expressed in both prokaryotic and eukaryotic cell types. For those TIAP's which increase apoptosis it may be desirable to express the protein under control of an inducible promoter for the purposes of protein production.

In general, TIAP proteins according to the invention may be produced by transformation of a suitable host cell with all or part of a TIAP-encoding DNA fragment (e.g., the cDNA described herein) in a suitable expression vehicle.

Those skilled in the field of molecular biology will understand that any of a wide variety of expression systems may be used to provide the recombinant protein. The precise host cell used is not critical to the invention. The TIAP protein may be produced in a prokaryotic host (e.g., *E. coli*) or in a eukaryotic host (e.g., *Saccharomyces cerevisiae*, insect cells, e.g., Sf21 cells, or mammalian cells, e.g., COS 1, NIH 3T3, or HeLa cells). Such cells are available from a wide range of sources (e.g., the American Type Culture Collection, Rockland, Md.; also, see, e.g., Ausubel et al., *Current Protocols in Molecular Biology*, John Wiley & Sons, New York, 1994). The method of transformation or transfection and the choice of expression vehicle will depend on the host system selected. Transformation and transfection methods are described, e.g., in Ausubel et al., (supra); expression vehicles may be chosen from those provided, e.g., in *Cloning Vectors: A Laboratory Manual* (Pouwels et al., 1985, Supp. 1987).

One preferred expression system is the baculovirus system (using, for example, the vector pBacPAK9) available from Clontech (Palo Alto, Calif.). If desired, this system may be used in conjunction with other protein expression techniques, for example, the myc tag approach described by Evan et al. (Mol. Cell Biol. 5: 3610, 1985).

Alternatively, a TIAP protein is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the TIAP protein is cloned into an expression vector which includes the dihydrofolate reductase (DHFR) gene. Integration of the plasmid and, therefore, the TIAP protein-encoding gene, into the host cell chromosome is selected for by inclusion of 0.01–300 $\mu$M methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR⁻ cells, ATCC Accession No. CRL 9096) are among the host cells preferred for DHFR selection of a stably-transfected cell line or DHFR-mediated gene amplification.

Once the recombinant TIAP protein is expressed, it is isolated, e.g., using affinity chromatography. In one example, an anti-TIAP protein antibody (e.g., produced as described herein) may be attached to a column and used to isolate the TIAP protein. Lysis and fractionation of TIAP protein-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Polypeptides of the invention, particularly short TIAP protein fragments, can also be produced by chemical synthesis (e.g., by the methods described in *Solid Phase Peptide Synthesis*, 2nd ed., 1984, The Pierce Chemical Co., Rockford, Ill.).

These general techniques of polypeptide expression and purification can also be used to produce and isolate useful TIAP fragments or analogs (described herein).

IV. Anti-TIAP Antibodies

To generate TIAP-specific antibodies, a TIAP coding sequence can be expressed as a C-terminal fusion with glutathione S-transferase (GST) (Smith et al., Gene 67: 31, 1988). The fusion protein can be purified on glutathione-Sepharose beads, eluted with glutathione cleaved with thrombin (at the engineered cleavage site), and purified to the degree necessary for immunization of rabbits. Primary immunizations can be carried out with Freund's complete adjuvant and subsequent immunizations with Freund's incomplete adjuvant. Antibody titres are monitored by Western blot and immunoprecipitation analyses using the thrombin-cleaved TIAP protein fragment of the GST-TIAP fusion protein. Immune sera are affinity purified using CNBr-Sepharose-coupled TIAP protein. Antiserum specificity is determined using a panel of unrelated GST proteins (including GSTp53, Rb, HPV-16 E6, and E6-AP) and GST-trypsin (which was generated by PCR using known sequences).

As an alternate or adjunct immunogen to GST fusion proteins, peptides corresponding to relatively unique hydrophilic regions of TIAP may be generated and coupled to keyhole limpet hemocyanin (KLH) through an introduced C-terminal lysine. Antiserum to each of these peptides is similarly affinity purified on peptides conjugated to BSA, and specificity tested in ELISA and Western blots using peptide conjugates, and by Western blot and immunoprecipitation using TIAP expressed as a GST fusion protein.

Alternatively, monoclonal antibodies may be prepared using the TIAP proteins described above and standard hybridoma technology (see, e.g., Kohler et al., Nature 256: 495, 1975; Kohler et al., Eur. J. Immunol. 6: 511, 1976; Kohler et al., Eur. J. Immunol. 6: 292, 1976; Hammerling et al., In *Monoclonal Antibodies and T Cell Hybridomas*, Elsevier, N.Y., 1981; Ausubel et al., supra). Once produced, monoclonal antibodies are also tested for specific TIAP recognition by Western blot or immunoprecipitation analysis (by the methods described in Ausubel et al., supra). Antibodies which specifically recognize TIAP are considered to be useful in the invention; such antibodies may be used, e.g., in an immunoassay to monitor the level of TIAP produced by a mammal (for example, to determine the amount or subcellular location of TIAP).

Preferably, antibodies of the invention are produced using fragments of the TIAP protein which lie outside highly conserved regions and appear likely to be antigenic. Antigenicity may be determined using criteria provided by the peptide structure program of the Genetics Computer Group Sequence Analysis Package (Program Manual for the GCG Package, Version 7, 1991) using the algorithm of Jameson and Wolf (CABIOS 4: 181, 1988), for example. In one specific example, such fragments are generated by standard techniques of PCR and cloned into the pGEX expression vector (Ausubel et al., supra). Fusion proteins are expressed in *E. coli* and purified using a glutathione agarose affinity matrix as described in Ausubel et al. (supra). To attempt to minimize the potential problems of low affinity or specificity of antisera, two or three such fusions are generated for each protein, and each fusion is injected into at least two rabbits. Antisera are raised by injections in a series, preferably including at least three booster injections.

V. Cloning of Additional TIAP Genes

Low stringency Southern blot hybridization of human genomic using probes specific for TIAP show bands which correspond to the other IAP nucleotide sequences, both known and unknown. This result indicates that additional TIAP sequences may be readily identified using low stringency hybridization. Standard techniques including PCR and hybridization may be used to clone homologues and additional genes.

VI. Characterization of TIAP Apoptosis Modulating Activity

The apoptosis inhibiting capability of TIAPs can be defined in an in vitro system known to detect alterations in apoptosis. Mammalian expression constructs carrying TIAPs and their truncated forms can be introduced into various cell lines such as CHO, NIH 3T3, HL60, Rat-1, or Jurkat cells, for example. In addition, SF21 insect cells may be used in which case the TIAP gene is preferentially expressed using an insect heat shock promoter. Apoptosis will then be induced in transfected and control cells employing standard methodologies (e.g. serum withdrawal and staurosporine). A survival index (ratio of surviving transfected cells to surviving control cells) will indicate the strength of each TIAP construct in inhibiting apoptosis. These experiments can confirm the presence of apoptosis inhibiting or enhancing activity and, can help to determine the minimal functional region of an TIAP. These methods may also be used in combination with compounds to identify compounds which modulate apoptosis via their effect on TIAP expression.

Specific examples of apoptosis assays are provided in the following references:

Fibroblasts: Vossbeck et al., Int. J. Cancer 61: 92, 1995); Goruppi et al., Oncogene 9: 1537, 1994; Fernandez et al., Oncogene 9: 2009, 1994; Harrington et al., EMBO J. 13: 3286, 1994; and Itoh et al, J. Biol. Chem. 268: 10932, 1993.

Insect Cells: Clem et al., Science 254: 1388, 1991; Crook et al., J. Virol. 67: 2168, 1993; Rabizadeh et al., J. Neurochem 61: 2318, 1993; Birnbaum et al., J. Virol. 68: 2521, 1994; and Clem et al., Mol. Cell. Biol. 14: 5212, 1994.

VII. Identification of Compounds That Modulate TIAP Protein Expression

Based on our experimental results, we have developed a number of screening procedures for identifying therapeutic compounds (e.g., anti-apoptotic or apoptosis-inducing compounds) which can be used in patients, including both warm- and cold-blooded animals. In particular examples, compounds that up-regulate or activate TIAP proteins are considered useful in the invention for treatment of conditions hallmarked by an excessive amount of apoptosis, such as male infertility caused by low sperm count. Similarly, compounds that down-regulate or inhibit TIAP proteins are also considered useful as drugs for the treatment of diseases hallmarked by impaired apoptosis, such as cancer. In addition, such a TIAP-inhibiting compound may be employed for use as a male birth control. In general, the screening methods of the invention involve screening any number of compounds for therapeutically active agents by employing any number of in vitro or in vivo experimental systems.

The methods of the invention simplify the evaluation, identification, and development of active agents for the treatment and prevention of conditions involving an inappropriate amount of apoptosis, which may be excessive or insufficient, depending upon the condition. These screening methods provide a facile means for selecting natural product extracts or compounds of interest from a large population which are further evaluated and condensed to a few active and selective materials. Constituents of this pool are then purified and evaluated in the methods of the invention to determine their anti-apoptotic or apoptotic-inducing activities.

In general, novel drugs for the treatment of conditions involving an appropriate level of apoptosis are identified from large libraries of both natural product or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic-, or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-apoptotic or apoptotic-inducing activities should be employed whenever possible.

When a crude extract is found to have anti-apoptotic or apoptotic-inducing activities or both, further fractionation of the positive lead extract is necessary to isolate chemical constituents responsible for the observed effect. Thus, the goal of the extraction, fractionation, and purification process is the careful characterization and identification of a chemical entity within the crude extract having anti-apoptotic or apoptotic-inducing activities. The same in vivo and in vitro assays described herein for the detection of activities in mixtures of compounds can be used to purify the active component and to test derivatives thereof. Methods of fractionation and purification of such heterogenous extracts are known in the art. If desired, compounds shown to be useful agents for the treatment of pathogenicity are chemically modified according to methods known in the art. Compounds identified as being of therapeutic value are subsequently analyzed using any standard animal model of degenerative disease or cancer known in the art.

Below we describe screening methods for identifying and evaluating the efficacy of a compound as an anti-apoptotic or apoptotic-inducing agent. These methods are intended to illustrate, not limit, the scope of the claimed invention.

a) Screens for Compounds Affecting TIAP Protein Expression

TIAP cDNAs may be used to facilitate the identification of compounds that increase or decrease TIAP protein expression. In one approach, candidate compounds are added, in varying concentrations, to the culture medium of cells (e.g., germ-line cells) expressing TIAP mRNA. The TIAP mRNA expression is then measured, for example, by Northern blot analysis (Ausubel et al., supra) using a TIAP DNA, or cDNA or RNA fragment, as a hybridization probe. The level of TIAP mRNA expression in the presence of the candidate compound is compared to the level of TIAP mRNA expression in the absence of the candidate compound, all other factors (e.g., cell type and culture conditions) being equal.

Alternatively, or in addition, candidate compounds may be screened for those which modulate TIAP apoptosis inhibiting activity. In this approach, the degree of apoptosis in the presence of a candidate compound is compared to the degree of apoptosis in its absence, under equivalent conditions. Again, such a screen may begin with a pool of candidate compounds, from which one or more useful modulator compounds are isolated in a step-wise fashion. Apoptosis activity may be measured by any standard assay, for example, those described herein.

Candidate TIAP modulators include peptide as well as non-peptide molecules (e.g., peptide or non-peptide molecules found, e.g., in a cell extract, mammalian serum, or growth medium on which mammalian cells have been cultured).

A compound which promotes an increase in TIAP expression or TIAP activity is considered particularly useful in the invention; such a molecule may be used, for example, as a therapeutic to increase cellular levels of TIAP and thereby exploit the effect of TIAP polypeptides for the inhibition of apoptosis.

Modulators found to be effective at the level of TIAP expression or activity may be confirmed as useful in animal models and, if successful, may be used as anti-cancer therapeutics for either the inhibition or the enhancement of apoptosis, as appropriate.

The effect of candidate compounds on TIAP-mediated apoptosis may, instead, be measured at the level of translation by using the general approach described above with standard protein detection techniques, such as Western blotting or immunoprecipitation with a TIAP-specific antibody.

In one approach to detect compounds which regulate TIAP at the level of transcription, candidate compounds may be tested for an ability to regulate a reporter gene whose expression is directed by a TIAP gene promoter. For example, a cell unlikely to undergo apoptosis may be transfected with a expression plasmid that includes a luciferase reporter gene operably linked to the TIAP promoter. Candidate compounds may then be added, in varying concentrations, to the culture medium of the cells. Luciferase expression levels may then be measured by subjecting the compound-treated transfected cells to standard luciferase assays known in the art, such as the luciferase assay system kit used herein that is commercially available from Promega (Madison, Wis.), and rapidly assessing the level of luciferase activity on a luminometer. The level of luciferase expression in the presence of the candidate compound is compared to the level of luciferase expression in the absence of the candidate compound, all other factors (e.g., cell type and culture conditions) being equal.

Compounds that modulate the level of TIAP protein expression may be purified, or substantially purified, or may be one component of a mixture of compounds such as an extract or supernatant obtained from cells, from mammalian serum, or from growth medium in which mammalian cells have been cultured (Ausubel et al., supra). In an assay of a mixture of compounds, TIAP protein expression is tested against progressively smaller subsets of the compound pool (e.g., produced by standard purification techniques such as HPLC or FPLC) until a single compound or minimal number of effective compounds is demonstrated to modulate TIAP protein expression.

b) Screens for Compounds Affecting TIAP Biological Activity

Compounds may also be screened for their ability to modulate apoptosis. Changes in the level of TIAP-induced inhibition of apoptosis may be used for such screens. In this approach, the degree of apoptosis in the presence of a candidate compound is compared to the degree of apoptosis in its absence, under equivalent conditions. Again, the screen may begin with a pool of candidate compounds, from which one or more useful modulator compounds are isolated in a step-wise fashion. Apoptosis activity may be measured by any standard assay, for example, those described herein.

Another method for detecting compounds that modulate the apoptosis-inhibiting activity of TIAP has been to screen for compounds that interact physically with the TIAP polypeptide. These compounds were detected by adapting yeast two-hybrid expression systems known in the art. These systems detected protein interactions using a transcriptional activation assay and are generally described by Gyuris et al. (Cell 75: 791, 1993) and Field et al. (Nature 340: 245, 1989), and are commercially available from Clontech (Palo Alto, Calif.). In addition, PCT Publication WO 95/28497 describes a yeast two-hybrid assay in which proteins involved in apoptosis, by virtue of their interaction with Bc1–2, were detected.

A compound that promotes an increase in the expression or biological activity of the TIAP protein is considered particularly useful in the invention; such a molecule may be used, for example, as a therapeutic to increase cellular levels of TIAP and thereby exploit the ability of TIAP polypeptides to inhibit apoptosis. This would be advantageous in the treatment of conditions, such as male infertility characterized low sperm count, in which there is an excessive amount of apoptosis.

A compound that decreases TIAP activity (e.g., by decreasing TIAP gene expression or TIAP biological activity) may also be used to decrease cellular proliferation. This would be advantageous in the treatment of testicular cancer.

Molecules that are found, by the methods described above, to effectively modulate TIAP gene expression or polypeptide activity may be tested further in animal models. If they continue to function successfully in an in vivo setting, they may be used as therapeutics to either inhibit or enhance apoptosis, as appropriate.

VIII. Detection of a Condition Involving Altered Apoptosis

TIAP polypeptides and nucleic acid sequences find diagnostic use in the detection or monitoring of conditions involving aberrant levels of apoptosis. For example, decreased expression of TIAP may be correlated with enhanced apoptosis in human testicular cells, which may result in reduced male fertility. Alternatively, increased expression of TIAP may be correlated with reduced apoptosis in testicular cells, and may indicate cancer, or a predisposition to develop cancer. Accordingly, a decrease or increase in the level of TIAP production may provide an indication of a deleterious condition. Levels of TIAP expression may be assayed by any standard technique. For example, TIAP expression in a biological sample (e.g., a biopsy) may be monitored by standard Northern blot analysis or may be aided by PCR (see, e.g., Ausubel et al., supra; *PCR Technology: Principles and Applications for DNA Amplification*, ed., H. A. Ehrlich, Stockton Press, NY; and Yap and McGee, Nucl. Acids. Res. 19: 4294, 1991).

Alternatively, a patient sample may be analyzed for one or more mutations in the TIAP sequences using a mismatch detection approach. Generally, these techniques involve PCR amplification of nucleic acid from the patient sample, followed by identification of the mutation (i.e., mismatch) by either altered hybridization, aberrant electrophoretic gel migration, binding or cleavage mediated by mismatch binding proteins, or direct nucleic acid sequencing. Any of these techniques may be used to facilitate mutant TIAP detection, and each is well known in the art; examples of particular techniques are described, without limitation, in Orita et al. (Proc. Natl. Acad. Sci. USA 86: 2766, 1989); and Sheffield et al (Proc. Natl. Acad. Sci. USA 86: 232, 1989).

In yet another approach, immunoassays are used to detect or monitor TIAP protein in a biological sample. TIAP-specific polyclonal or monoclonal antibodies (produced as described above) may be used in any standard immunoassay format (e.g., ELISA, Western blot, or RIA assay) to measure TIAP polypeptide levels; again comparison is to wild-type TIAP levels and a decrease in TIAP production is indicative of a condition involving increased apoptosis. Examples of immunoassays are described, e.g., in Ausubel et al, supra. Immunohistochemical techniques may also be utilized for TIAP detection. For example, a tissue sample may be obtained from a patient, and a section stained for the presence of TIAP using an anti-TIAP antibody and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, 1982) and Ausubel et al. (supra).

In one preferred example, a combined diagnostic method may be employed that begins with an evaluation of TIAP protein production (for example, by immunological techniques or the protein truncation test (Hogerrorst, F. B. L., et al., Nature Genetics 10: 208, 1995) and also includes a nucleic acid-based detection technique designed to identify more subtle TIAP mutations (for example, point mutations). As described above, a number of mismatch detection assays are available to those skilled in the art, and any preferred technique may be used (see above). By this approach, mutations in TIAP may be detected that either result in loss of TIAP expression or loss of TIAP biological activity. In a variation of this combined diagnostic method, TIAP biological activity is measured as protease activity using any appropriate protease assay system (for example, those described above).

Mismatch detection assays also provide the opportunity to diagnose a TIAP-mediated predisposition to sterility or testicular cancer. For example, a male patient heterozygous for an TIAP mutation may show no clinical symptoms and yet possess a higher than normal probability of developing one or more types of testicular cancer, or developing problems in fertility. Given this diagnosis, a patient may take precautions to minimize their exposure to adverse environmental factors (for example, UV exposure or chemical mutagens) and to carefully monitor their medical condition (for example, through frequent physical examinations). This type of TIAP diagnostic approach may also be used to detect TIAP mutations in prenatal screens.

The TIAP diagnostic assays described above may be carried out using any biological sample (for example, any biopsy sample or bodily fluid or tissue) in which TIAP is normally expressed (for example, the testis). Identification of a mutant TIAP gene may also be assayed using these sources for test samples. Alternatively, a TIAP mutation, particularly as part of a diagnosis for predisposition to TIAP-associated conditions, may be tested using a DNA sample from any cell, for example, by mismatch detection techniques; preferably, the DNA sample is subjected to PCR amplification prior to analysis.

IX. TIAP Therapies

Therapies may be designed to circumvent or overcome a TIAP gene defect or inadequate TIAP gene expression, and thus modulate and possibly alleviate conditions involving an inappropriate amount of apoptosis. In considering various therapies, it is understood that such therapies may be targeted at any tissues demonstrated to express TIAP (e.g., the testis). In particular, therapies to inhibit TIAP gene expression are useful in promoting apoptosis in cancerous cells, or are useful as a male birth control method. Apoptosis-inducing TIAP reagents may include, without limitation, mutant or fragment TIAP polypeptides, TIAP antisense RNA, or any compound which decreases TIAP apoptosis-inhibiting activity.

Furthermore, because the expression levels of TIAP genes correlate with the levels of apoptosis, the TIAP gene also finds use in anti-apoptosis gene therapy. In particular, to sustain spermatogenesis, a functional TIAP gene may be introduced into cells in the testis predicted to undergo undesirable apoptosis (for use in, for example, male patients suffering from infertility).

a) Protein Therapy

Treatment or prevention of inappropriate apoptosis can be accomplished by replacing mutant or surplus TIAP protein with normal protein, by modulating the function of mutant protein, or by delivering normal TIAP protein to the appropriate cells (e.g., germ-line cells). It is also be possible to modify the pathophysiologic pathway (e.g., an apoptotic signal transduction pathway) in which the protein participates in order to correct the physiological defect.

To replace a mutant protein with normal protein, or to add protein to cells (e.g., germ-line cells) which no longer express sufficient TIAP, it is necessary to obtain large amounts of pure TIAP protein from cultured cell systems which can express the protein. Delivery of the protein to the affected tissues (e.g., tissue in infertile male patients) can then be accomplished using appropriate packaging or administrating systems. Alternatively, small molecule analogs may be used and administered to act as TIAP agonists and in this manner produce a desired physiological effect. Methods for finding such molecules are provided herein.

b) Gene Therapy

Gene therapy is another potential therapeutic approach in which normal copies of the TIAP gene or nucleic acid encoding TIAP antisense RNA are introduced into selected tissues to successfully encode for normal and abundant protein or TIAP antisense RNA in cells which inappropriately either suppress cell death (e.g., cancerous testicular cells) or enhance the rate of cell death (e.g., spermatocytes which prematurely apoptose), respectively. The gene must be delivered to those cells in a form in which it can be taken up and encode for sufficient protein to provide effective function. Alternatively, in some mutants it may be possible to promote apoptosis by introducing another copy of the homologous gene bearing a second mutation in that gene or to alter the mutation, or use another gene to block any negative effect.

Transducing retroviral vectors can be used for somatic cell gene therapy especially because of their high efficiency of infection and stable integration and expression. The targeted cells however must be able to divide and the expression levels of normal protein should be high. For example, the full length TIAP gene, or portions thereof, can be cloned into a retroviral vector and driven from its endogenous promoter or from the retroviral long terminal repeat or from a promoter specific for the target cell type of interest (such as spermatocytes). Other viral vectors which can be used include adenovirus, adeno-associated virus, vaccinia virus, bovine papilloma virus, or a herpes virus such as Epstein-Barr Virus.

Gene transfer could also be achieved using non-viral means requiring infection in vitro. This would include calcium phosphate, DEAE dextran, electroporation, and protoplast fusion. Liposomes may also be potentially beneficial for delivery of DNA into a cell. Although these methods are available, many of these are lower efficiency.

Transplantation of normal genes into the affected cells (e.g., germ-line cells) of a patient can also be useful therapy. In this procedure, a normal TIAP gene is transferred into a cultivatable cell type, either exogenously or endogenously to the patient. These cells are then injected serotologically into the targeted tissue(s).

Retroviral vectors, adenoviral vectors, adenovirus-associated viral vectors, or other viral vectors with the appropriate tropism for testicular cells likely to be involved in apoptosis (for example, spermatocytes) may be used as a gene transfer delivery system for a therapeutic TIAP gene construct. Numerous vectors useful for this purpose are generally known (Miller, A. D., Human Gene Therapy 1: 5, 1990; Friedmann, T., Science 244: 1275, 1989; Eglitis and Anderson, BioTechniques 6: 608, 1988; Tolstoshev and Anderson, Curr. Opin. Biotech. 1: 55, 1990; Cornetta et al., Nucl. Acid Res. and Mol. Biol. 36: 311, 1987; Anderson, W. F., Science 226: 401, 1984; Moen, R. C., Blood Cells 17: 407, 1991; Miller et al., Biotech. 7: 980, 1989; Le Gal La Salle et al., Science 259: 988, 1993; and Johnson, L. G., Chest 107: 77S, 1995). Retroviral vectors are particularly well developed and have been used in clinical settings (Rosenberg et al., New Engl. J. Med. 323: 370, 1990; Anderson et al., U.S. Pat. No. 5,399,346).

Non-viral approaches may also be employed for the introduction of therapeutic DNA into cells (e.g., germ-line cells) otherwise predicted to undergo apoptosis. For example, TIAP may be introduced into a testicular cell by lipofection (Felgner et al., Proc. Natl. Acad. Sci. USA 84: 7413, 1987; Ono et al., Neurosci. Lett. 117: 259, 1990; Brigham et al., Am. J. Med. Sci. 298: 278, 1989; Staubinger et al., Meth. Enz. 101: 512, 1983); asialorosonucoid-polylysine conjugation (Wu et al., J. Biol. Chem. 263: 14621, 1988; Wu et al., J. Biol. Chem. 264: 16985, 1989); or, less preferably, micro-injection under surgical conditions (Wolff et al., Science 247: 1465, 1990).

In another approach that may be utilized with all of the above methods, a therapeutic TIAP DNA construct is preferably applied to the site of the desired apoptosis event (for example, by injection). However, the therapeutic construct may also be applied to tissue in the vicinity of the desired apoptosis event or to a blood vessel supplying the cells (e.g., cancerous cells) desired to undergo apoptosis.

In the constructs described, TIAP cDNA expression can be directed from any suitable promoter (e.g., the human cytomegalovirus (CMV), simian virus 40 (SV40), or met-allothionein promoters), and regulated by any appropriate mammalian regulatory element. For example, if desired, enhancers known to preferentially direct gene expression in spermatocytes, or other testicular cells may be used to direct TIAP expression. The enhancers used could include, without limitation, those that are characterized as tissue- or cell-specific in their expression. Alternatively, if a TIAP genomic clone is used as a therapeutic construct (for example, following isolation by hybridization with the TIAP cDNA described above), regulation may be mediated by the cognate regulatory sequences or, if desired, by regulatory sequences derived from a heterologous source, including any of the promoters or regulatory elements described above.

Less preferably, TIAP gene therapy is accomplished by direct administration of the TIAP mRNA to a cell (e.g., a germ-line cell) predicted to undergo apoptosis. This mRNA may be produced and isolated by any standard technique, but is most readily produced by in vitro transcription using a TIAP cDNA under the control of a high efficiency promoter (e.g., the T7 promoter). Administration of TIAP mRNA to malignant cells is carried out by any of the methods for direct nucleic acid administration described above.

Ideally, the production of TIAP protein by any gene therapy approach described above results in a cellular level of TIAP that is at least equivalent to the normal, cellular level of TIAP in an unaffected individual. Treatment by any TIAP-mediated gene therapy approach may be combined with more traditional therapies.

Antisense based strategies have employed to explore TIAP gene function and as a basis for therapeutic drug design. The principle is based on the hypothesis that sequence-specific suppression of gene expression can be achieved by intracellular hybridization between mRNA and a complementary antisense species. The formation of a hybrid RNA duplex may then interfere with the processing/transport/translation and/or stability of the target TIAP mRNA. Antisense strategies may use a variety of approaches including the use of antisense oligonucleotides and injection of antisense RNA. For our analysis of TIAP gene function, we employed the method of transfection of antisense RNA expression vectors into targeted cells. Antisense effects can be induced by control (sense) sequences, however, the extent of phenotypic changes are highly variable. Phenotypic effects induced by antisense effects are based on changes in criteria such as protein levels, protein activity measurement, and target mRNA levels.

For example, TIAP gene therapy may also be accomplished by direct administration of antisense TIAP mRNA to a cell (e.g., a germ-line cell) that is expected to undergo undesired apoptosis. The antisense TIAP mRNA may be produced and isolated by any standard technique, but is most readily produced by in vitro transcription using an antisense TIAP cDNA under the control of a high efficiency promoter (e.g., the T7 promoter). Administration of antisense TIAP mRNA to cells can be carried out by any of the methods for direct nucleic acid administration described above.

Another therapeutic approach within the invention involves administration of recombinant TIAP polypeptide, either directly to the site of a desired apoptosis event (for example, by injection) or systemically (for example, by any conventional recombinant protein administration technique). The dosage of TIAP depends on a number of factors, including the size and health of the individual patient, but, generally, between 0.1 mg and 100 mg inclusive are administered per day to an adult in any pharmaceutically acceptable formulation.

X. Administration of TIAP Polypeptides, TIAP Genes, or Modulators of TIAP Synthesis or Function A TIAP protein, gene, or modulator may be administered with a pharmaceutically-acceptable diluent, carrier, or excipient, in unit dosage form. Conventional pharmaceutical practice may be employed to provide suitable formulations or compositions to administer TIAP to patients suffering from or presymptomatic for a TIAP-associated testicular carcinoma. Any appropriate route of administration may be employed, for example, parenteral, intravenous, subcutaneous, intramuscular, intraspinal, or oral administration. Therapeutic formulations may be in the form of liquid solutions or suspensions; for oral administration, formulations may be in the form of tablets or capsules.

Methods well known in the art for making formulations are found in, for example, *Remington's Pharmaceutical Sciences*, (18th edition), ed. A. Gennaro, 1990, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for TIAP modulatory compounds include ethylene-vinyl acetate copolymer particles, suppositories, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a TIAP protein, gene, or modulatory compound may be combined with more traditional therapies for the condition, such as surgery, radiation, or chemotherapy for cancer.

XI. TIAP-mediated Male Birth Control

A compound known to increase apoptosis in testicular cells (e.g., a compound that decreases TIAP activity) may be administered to a male patient to reversibly reduce sperm cell count and, therefore, reduce fertility. It will be understood that the compound will be administered with a pharmaceutically acceptable carrier and target the more developed sperm cell progenitors, and not the totipotent spermatogonium cell.

Alternatively, a compound known to increase TIAP activity may be administered to a male patient to reversibly increase sperm cell count. Such administration is useful in human patients suffering from low sperm cell titers, as well as commercially (or otherwise) important animals suffering from low reproduction rates. For example, the current decline in alligator reproduction rates in Florida is thought to be due to a decline in sperm cell counts in male alligators. Supplementing alligator food with a compound which specifically increases TIAP activity may remedy this situation. Since TIAP is testes specific, the compound will have no effect on female alligators consuming the supplemented food.

XII. Testes-specific Administration

The testes-specific promoter sequence of the TIAP gene, which overlaps SEQ ID NO: 5 (FIG. 6), allows the administration of compounds that specifically target the testes. For example, in patients with a lethal testicular cancer, it may be desirable to destroy all testicular cells in a less invasive method than surgical removal of the testes. In this example, the TIAP gene promoter may be operably linked to, for example, a nucleic acid molecule encoding a toxic protein (e.g., cholera toxin or diptheria toxin). This toxic protein will be produced, and, thus, destroy, all testicular cells, but will not be produced in (or have any adverse effect upon) any other tissue types.

XIII. Construction of a Transgenic Mammal

Characterization of TIAPs can provide information that allows for the development of an TIAP knockout mouse model by homologous recombination (or an TIAP overproducing mouse by other means of integration). A replacement type targeting vector can be constructed using an isogenic genomic clone from a mouse strain, e.g. 129/Sv (Strategene, LaJolla, Calif.). The targeting vector will be introduced into a J1 line of embryonic stem (ES) cells by electroporation to generate ES cell lines that carry a profoundly truncated form of an TIAP. To generate chimeric founder mice, the targeted cell lines will be injected into a mouse blastula stage embryo. Heterozygote offspring will be interbred to homozygosity. Knockout mice may be constructed as a means of screening in vivo for therapeutic compounds which modulate apoptosis.

In addition, the promoter of the TIAP gene (overlapping SEQ ID NO: 5) is also useful for generating transgenic mice with alterations localized to the testes tissue. For example, in mice having known male sterility genetic defects, an anti-apoptosis gene (e.g., TIAP) may be over-expressed in a testes-specific manner to overcome the genetic lesion. Since the promoter is testes-specific, the female transgenic mice will show no effects of the transgene.

The following examples are meant to illustrate, but not limit, the invention.

EXAMPLE I

Identification of TIAP

The adult testis is an organ in which apoptosis plays a major role in the maintenance of cellular homeostasis and fidelity of spermatogenesis. In the testis, up to 75% of male germ cells undergo apoptosis, possibly as a mechanism by which defective germ cells are eliminated (Hsueh et al., supra). The molecular mechanisms of this programmed cell death, however, remain largely unknown (Furuchi et al., supra). Thus, during the characterization of the X-linked IAP (XIAP; a recently cloned novel inhibitor of apoptosis), the presence of a second transcript in the testis was immediately intriguing.

Figure 2:
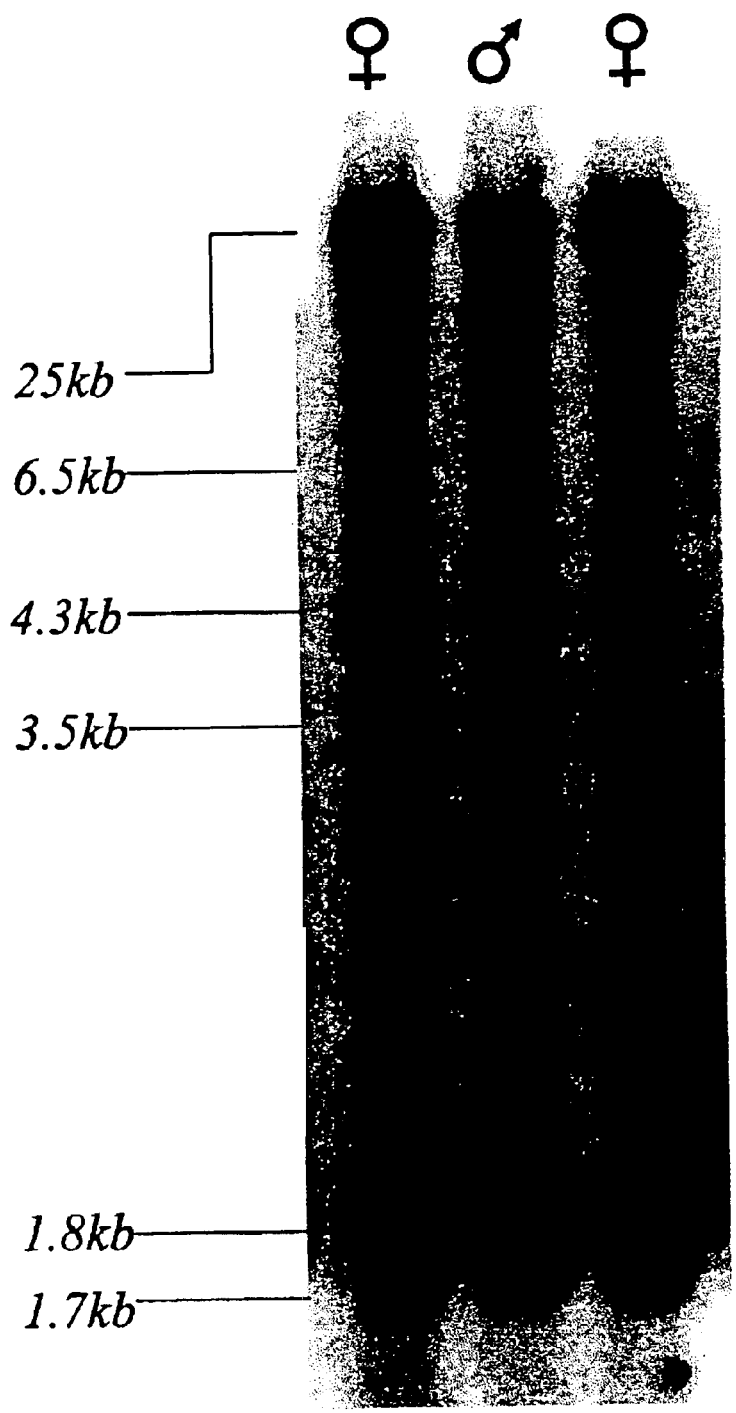
FIG. 2 is a Southern blotting analysis showing the XIAP cDNA-hybridizing bands in EcoRI-digested human genomic DNA. Human genomic DNA was digested with EcoRI and resolved on a 1% agarose gel. Following transfer to a nitrocellulose membrane, the gel was probed with a full length XIAP coding region probe, and six bands were found to hybridize. Two of the bands (of approximately 25 kb and 3.5 kb in size) correspond to the X-linked XIAP gene, while the 1.7 kb band corresponds to the testes specific IAP (TIAP) gene. Note that the XIAP bands appear at twice the intensity in the female DNA compared to the male DNA. This is consistent with the dose of X chromosome present.

XIAP cDNA sequences were used to probe blots of human genomic DNA digested with EcoRI and to probe a multiple tissue northern (MTN) blot of human polyadenylated RNA. The results of these screens are shown in FIGS. 2 and 3, respectively. Six discrete bands, of approximately 25 kb, 6.5 kb, 4.3 kb, 3.5 kb, 1.8 kb, and 1.7 kb in size, showed up on the genomic blot (FIG. 2), while the multiple tissue northern blot showed ubiquitous expression of a 9.5 kb message with a second smaller transcript (approximately 2.2 kb) present in the testes (FIG. 3).

Genomic and cDNA lambda phage libraries were screened using probes generated from the existing XIAP cDNA sequence. The libraries and the appropriate host cells used in the screen are listed in Table I.

TABLE I

| Library | Vector | Supplier | Type | Host |
|---|---|---|---|---|
| Human male placenta | ZAP | Stratagene | Genomic | XL1-Blue MRA |
| Human spinal cord | gt10 | ClonTech | cDNA | C600Hfl |
| Human liver | ZAP | Stratagene | cDNA | XL1-Blue MRA |
| Human testes | gt11 | ClonTech | cDNA | Y1090r- |

EXAMPLE II

The TIAP Gene

Southern blotting analysis of genomic phage clone DNA was used to generate phage contigs and a restriction map of the XIAP locus. Five distinct loci were isolated, with XIAP-reactive EcoRI fragments corresponding to all six bands seen on the Southern blot of genomic DNA. The largest locus (containing the 25 kb and 3.5 kb bands on the Southern blot) was determined to contain the functional X-linked XIAP gene based on sequence from coding region primers and probing with different coding region and UTR probes. The remaining four loci were analysed to a lesser extent. The results of this analysis are shown in Table II

TABLE II

| Genomic EcoRI fragment size | Identity | Reasoning |
|---|---|---|
| 25 kb | xiap promoter through BIR2 | Sequence analysis. |
| 6.5 kb | pseudogene | Weakly hybridizes with BIR1 of xiap but nothing else. |
| 4.3 kb | pseudogene (likely an incomplete, reverse transcribed copy of xiap). | Sequencing showed homology with xiap from 3'UTR up to BIR2 at which point the homology ended. There were in-frame stop codons within the coding region. |
| 3.5 kb | xiap BIR2 to the end. | Sequence analysis. |
| 1.8 kb | pseudogene | Sequencing showed homology to 3' half of xiap. There were many frame shifts in the sequence. |
| 1.7 kb | testes specific transcript | Described below. |

EXAMPLE III

TIAP cDNA

Figure 4A:
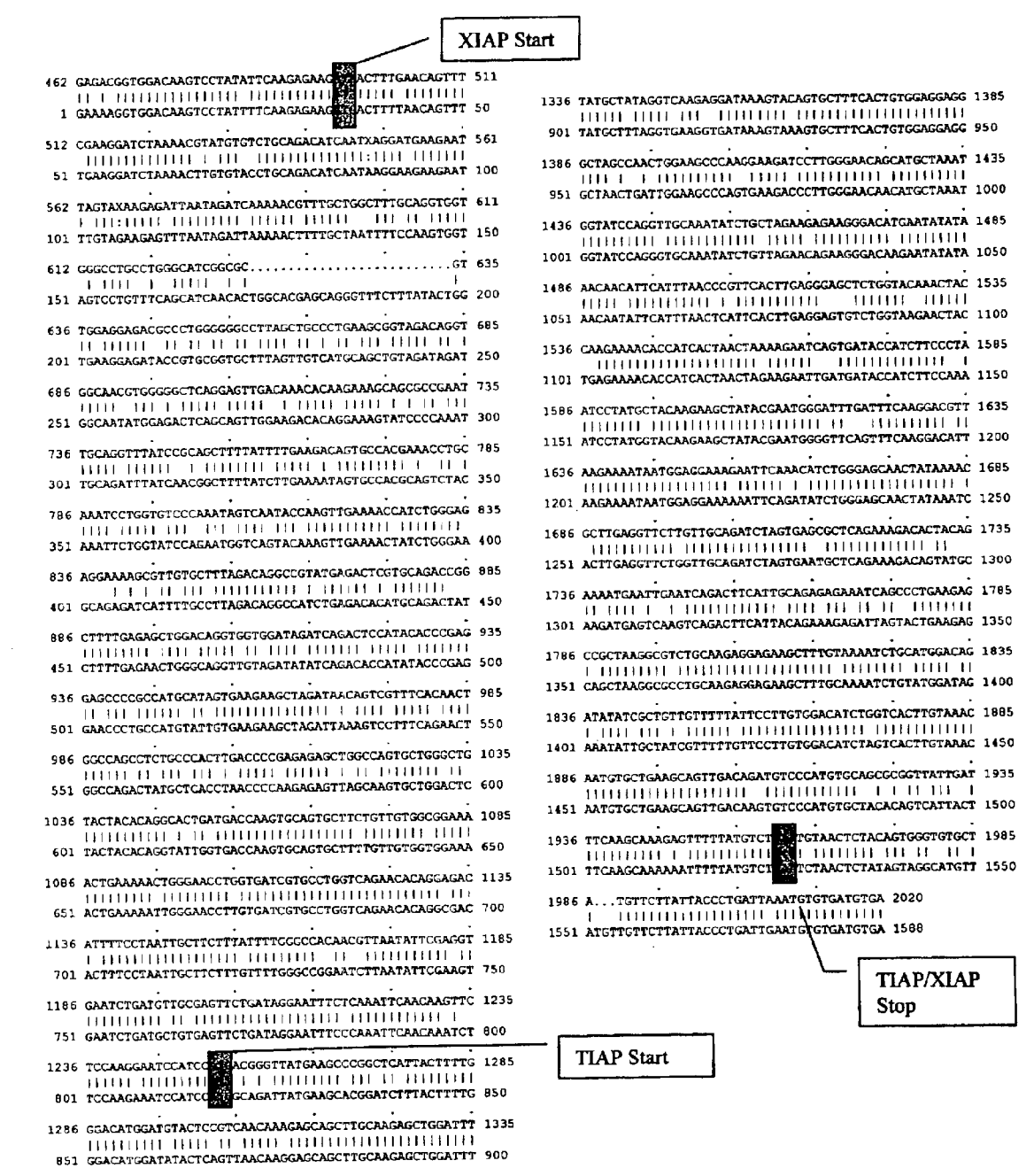
Figure 5:
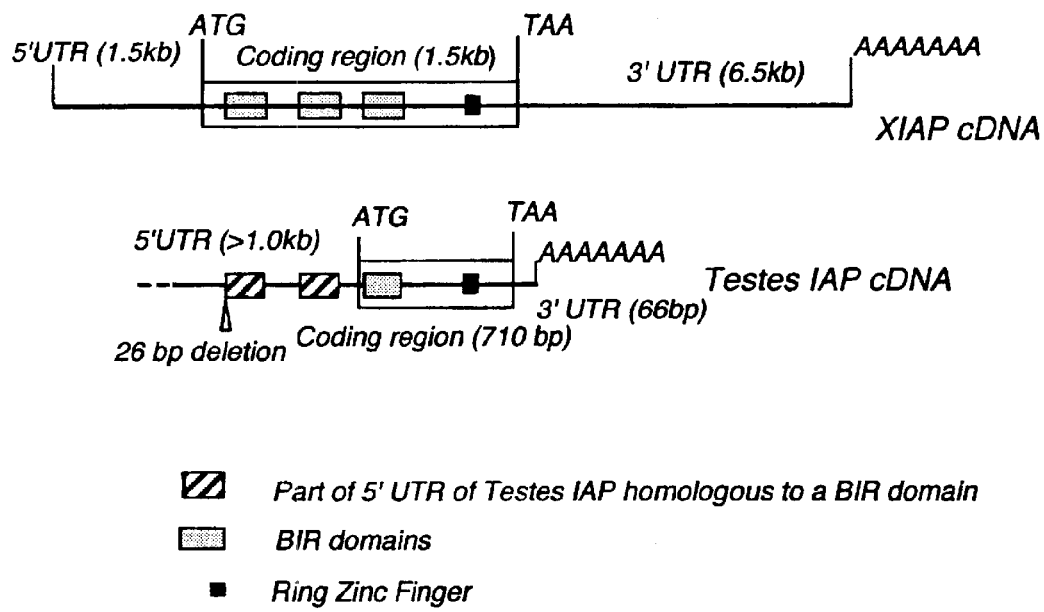
FIG. 5 is a schematic diagram showing the comparison of the cDNA structures of XIAP (top) and Testis IAP (TIAP; bottom). BIR domains are shown as large white boxes; ring zinc fingers are shown as smaller black boxes, and region of the TIAP gene that are homologous to a BIR domain but are not within the putative coding region are shown as cross-hatched boxes. The putative TIAP protein is homologous to the last BIR domain of XIAP through to the end of the ring zinc finger.

On a human multiple tissue northern (MTN) blot of poly-$A^+$ RNA, a 9.5 kb XIAP-reactive band appeared to be ubiquitously expressed in all tissues tested with minor variations in intensity. Of note, however, was a second band of approximately 2 kb in size that appeared only in the testes. To investigate the possibility of a second form of XIAP expressed in the testes, a human testes cDNA library was screened with full length XIAP coding region probe. Interestingly, several clones isolated bore only 75–85% similarity with existing XIAP cDNA sequence. Overlapping clones from this testes specific cDNA were sequenced and compared with the XIAP sequence. Sequencing of the 2 kb band (FIG. 4A) indicates it potentially encodes a protein similar to XIAP (±80% identity; 90% similarity) that contains one BIR domain (corresponding to the third BIR domain of XIAP) and a carboxyl terminal RING zinc finger (FIG. 4B). Shown in FIG. 5 is a schematic diagram showing the comparison of the cDNA structures of XIAP and TIAP.

Figure 7B:
FIG. 7B is a Southern blotting analysis showing human genomic DNA digested with EcoRI and probed with a TIAP-specific 5'UTR probe. One prominent band of 1.7 kb hybridized with equal intensity in both males and females. Sequence of a genomic phage clone confirmed that this band corresponds to the TIAP cDNA isolated from the human testes cDNA library.
Figure 7A:
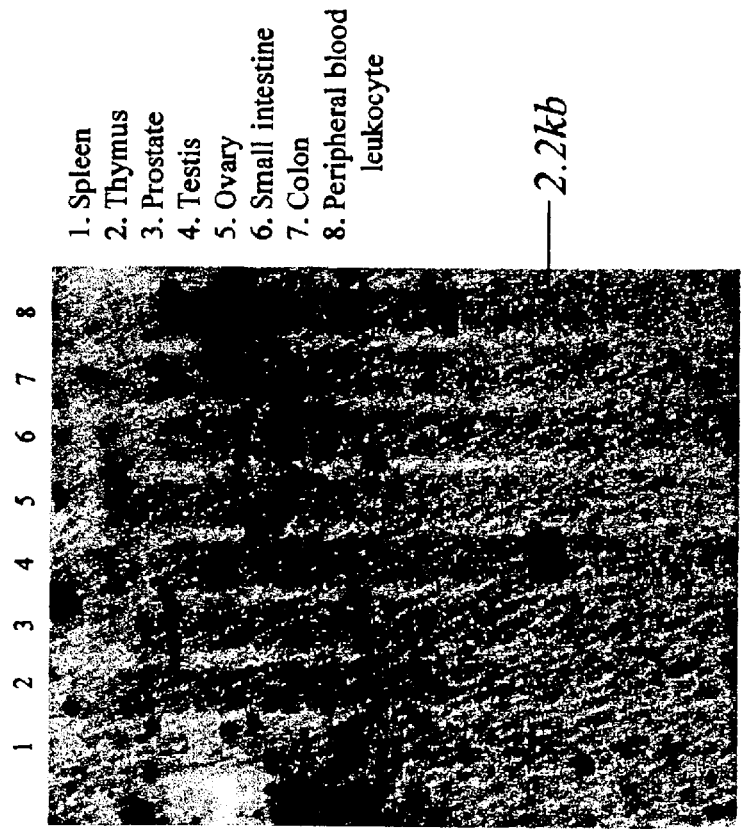
FIG. 7A is a Northern blotting analysis showing a human multiple tissue Northern blot (commercially available from Clontech Laboratories, Inc., Palo Alto, Calif.) probed with a TIAP-specific 5' UTR probe. The RNA of tissues probed are in the lanes as follows: 1, spleen; 2, thymus; 3, prostate; 4, testis; 5, ovary; 6, small intestine; 7, colon; 8, peripheral blood leukocyte. Only one band of 2.2 kb present in the testis hybridized with the probe.

To confirm that the clones isolated from the testes cDNA library represent the 2.2 kb transcript seen on the MTN blot, a region of the 5'UTR of TIAP (FIG. 6) with no significant homology to xiap was used to probe the original MTN blots (FIG. 7A). Only one band hybridized, and this one band corresponded to the 2.2 kb band in the testes. The same probe was used to probe a human genomic DNA blot and one prominent band showed up at approximately 1.7 kb (FIG. 7B). A genomic clone isolated from the XIAP screening was sequenced with testes-IAP specific primers and was found to contain the testes specific IAP locus. A portion of this phage clone was used in FISH analysis, which pinpointed the TIAP locus to chromosome 12, region q22–23.

EXAMPLE IV

Significance of TIAP

During and following meiosis of a spermatocyte, the X chromosome is inactivated (Richler et al., Nature Genetics 2: 192, 1992; Salido et al., Nature Genetics 2: 196, 1992). Thus, there must be some mechanism for X-linked genes required for the survival of the spermatocyte to evade inactivation. X-linked genes that are essential to the proper function of cells often have a duplicate copy present on an autosome and expressed specifically in the testes (e.g., PGK: Bluthmann et al., EMBO J. 1: 479, 1982; G6pd: Hendriksen et al., Genomics 41: 350, 1997; PDHA: Iannello et al., Reprod Fertil Dev 7: 705, 1995; PRPS: Taira et al., J. Biol Chem. 265: 16491, 1990; GKD: Sargent et al, Hum. Mol. Genet. 3: 1317, 1994). This duplicate copy is often present as an intronless gene whose expression is limited to cells of a germ-line origin. XIAP is a ubiquitously expressed anti-apoptotic protein and could very well have biological activity required for normal cell survival. TIAP, an autosomal (12q22–23) intronless gene expressed solely in the testes likely fills the role of XIAP in germ-line cells, where the xiap gene is either inactivated or absent.

Hence, since the role of TIAP is to substitute for XIAP in the spermatocytes and spermatids, TIAP may influence a wide variety of normal and disease effects. Furthermore, since TIAP is a functional homologue of XIAP, TIAP is likely to be anti-apoptotic.

Dysregulation of TIAP may result in a wide variety of pathologies. Both over- and under-expression of TIAP may lead to infertility. Too little TIAP may result in excessive apoptosis of developing sperm cells, leading to azospermia. Conversely, overexpression of TIAP may allow improperly differentiated sperm to escape a selection process, thus resulting in high levels of non-functional sperm cells. In addition, overexpression of TIAP may also lead to cancer, allowing the survival and proliferation of damaged cells that should normally die. Thus, overexpression of TIAP could be responsible for certain male germ line tumors.

Our evidence has revealed that the TIAP transcript seen in the testes forms a functional protein. Since the 5' untranslated region of the TIAP transcript is relatively long (FIG. 6), with many short potential upstream open reading frames, the typical ribosome scanning method of translational initiation likely cannot be used. Additionally, the homology of a large stretch of 5' UTR with BIR1/2 of XIAP would suggest that this sequence is not optimized for internal ribosome initiation, although little is known of the structural requirements for a mammalian IRES (internal ribosome entry site). It is not unusual, however, for non-standard transcription and/or translational machinery to be active in the male germ cells (Kleene, K. C., Mol. Reprod. Dev. 43: 268, 1996). For instance, examples exist of post-transcriptional modification of mRNA (e.g., Apolipoprotein), and start of translation from non-AUG start codons (e.g., PRPS3: Taira et al., supra).

Other Embodiments

In other embodiments, the invention includes any protein which is substantially identical to a mammalian TIAP polypeptide (FIG. 4B; SEQ ID NO: 2); such homologues include other substantially pure naturally-occurring mammalian TIAP proteins as well as allelic variants; natural mutants; induced mutants; DNA sequences which encode proteins and also hybridize to the TIAP DNA sequences of FIGS. 4A and 6 (SEQ ID NO: 1 and SEQ ID NO: 5) under high stringency conditions or, less preferably, under low stringency conditions; and proteins specifically bound by antisera directed to a TIAP polypeptide. The term also includes chimeric polypeptides that include a TIAP portion.

The invention further includes analogs of any naturally-occurring TIAP polypeptide. Analogs can differ from the naturally-occurring TIAP protein by amino acid sequence differences, by post-translational modifications, or by both. Analogs of the invention will generally exhibit at least 85%, more preferably 90%, and most preferably 95% or even 99% identity with all or part of a naturally-occurring TIAP amino acid sequence. The length of sequence comparison is at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring TIAP polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch, and Maniatis, *Molecular Cloning: A Laboratory Manual* (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition to full-length polypeptides, the invention also includes TIAP polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of TIAP polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events). Preferable fragments or analogs according to the invention are those which facilitate specific detection of a TIAP nucleic acid or amino acid sequence in a sample to be diagnosed.

All publications and patent applications mentioned in this specification are herein incorporated by reference to the same extent as if each independent publication or patent application was specifically and individually indicated to be incorporated by reference.

What is claimed is:

1. A method for identifying a compound that modulates inhibition by Testis IAP (TIAP), said method comprising the steps of:
   (a) providing an isolated polypeptide having at least 95% amino acid identity to human TIAP (SEQ ID NO: 2), wherein the polypeptide comprises a BIR domain and inhibits apoptosis;
   (b) contacting said TIAP polypeptide with a candidate compound; and
   (c) detecting binding between said candidate compound and said TIAP polypeptide, wherein a candidate compound that binds said TIAP polypeptide is identified as a compound that modulates inhibition of apoptosis by TIAP.

2. The method of claim 1, wherein said TIAP polypeptide has the sequence of SEQ ID NO: 2.

3. The method of claim 1, wherein said compound decreases apoptosis.

4. The method of claim 1, wherein said compound increases apoptosis.

* * * * *

SEQUENCE LISTING

```
<160> NUMBER OF SEQ ID NOS: 10

<210> SEQ ID NO 1
<211> LENGTH: 1559
<212> TYPE: DNA
<213> ORGANISM: Homo sapiens
<220> FEATURE:
```

```
<221> NAME/KEY: misc_feature
<222> LOCATION: (1)...(1559)
<223> OTHER INFORMATION: n = A,T,C or G

<400> SEQUENCE: 1
gagacggtgg acaagtccta tattcaagag aagataactt tgaacagttt cgaaggatct      60
aaaacgtatg tgtctgcaga catcaatnag gatgaagaat tagtanaaga gattaataga     120
tcaaaaacgt tgctggctt tgcaggtggt gggcctgcct gggcatcggc gcgttggagg      180
agacgccctg gggggcctta gctgccctga agcggtagac aggtggcaac gtggggctc      240 aggagttgac aaaacaaga aagcagcgcc gaattgcagg tttatccgca gcttttattt      300
tgaagacagt gccacgaaac ctgcaaatcc tggtgtccca aatagtcaat accaagttga     360
aaaccatctg ggagaggaaa agcgttgtgc tttagacagg ccgtatgaga ctcgtgcaga     420
ccggcttttg agagctggac aggtggtgga tagatcagac tccatacacc cgaggagccc     480
cgccatgcat agtgaagaag ctagataaca gtcgtttcac aactggccag cctctgccca     540
cttgaccccg agagagctgg ccagtgctgg gctgtactac acaggcactg atgaccaagt     600
gcagtgcttc tgttgtggcg aaaactgaa aaactgggaa cctggtgatc gtgcctggtc      660
agaacacagg agacattttc ctaattgctt cttatttttg ggccacaacg ttaatattcg     720
aggtgaatct gatgttgcga gttctgatag gaatttctca aattcaacaa gttctccaag     780
gaatccatcc atgacgggtt atgaagcccg gctcattact tttgggacat ggatgtactc     840
cgtcaacaaa gagcagcttg caagagctgg attttatgct ataggtcaag aggataaagt     900
acagtgcttt cactgtggag gaggctagc caactggaag cccaaggaag atccttggga     960
acagcatgct aaatggtatc caggttgcaa atatctgcta aagagaagg acatgaata      1020 tataaacaac attcatttaa cccgttcact tgagggagct ctggtacaaa ctaccaagaa     1080
aacaccatca ctaactaaaa gaatcagtga taccatcttc cctaatccta tgctacaaga     1140
agctatacga atgggatttg atttcaagga cgttaagaaa ataatggagg aaagaattca     1200
aacatctggg agcaactata aaacgcttga ggttcttgtt gcagatctag tgagcgctca     1260
gaaagacact acagaaaatg aattgaatca gacttcattg cagagagaaa tcagccctga     1320
agagccgcta aggcgtctgc aagaggagaa gctttgtaaa atctgcatgg acagatatat     1380
cgctgttgtt tttattcctt gtggacatct ggtcacttgt aaacaatgtg ctgaagcagt     1440
tgacagatgt cccatgtgca gcgcggttat tgatttcaag caaagagttt ttatgtctta     1500
atgtaactct acagtgggtg tgctatgttc ttattaccct gattaaatgt gtgatgtga     1559

<210> SEQ ID NO 2
<211> LENGTH: 236
<212> TYPE: PRT
<213> ORGANISM: Homo sapiens

<400> SEQUENCE: 2

Met Thr Gly Tyr Glu Ala Arg Leu Ile Thr Phe Gly Thr Trp Met Tyr
  1               5                  10                  15

Ser Val Asn Lys Glu Gln Leu Ala Arg Ala Gly Phe Tyr Ala Ile Gly
                 20                  25                  30

Gln Glu Asp Lys Val Gln Cys Phe His Cys Gly Gly Leu Ala Asn
             35                  40                  45

Trp Lys Pro Lys Glu Asp Pro Trp Glu Gln His Ala Lys Trp Tyr Pro
         50                  55                  60

Gly Cys Lys Tyr Leu Leu Glu Glu Lys Gly His Glu Tyr Ile Asn Asn
```

-continued

```
            65                  70                  75                  80
Ile His Leu Thr Arg Ser Leu Glu Gly Ala Leu Val Gln Thr Thr Lys
                    85                  90                  95

Lys Thr Pro Ser Leu Thr Lys Arg Ile Ser Asp Thr Ile Phe Pro Asn
            100                 105                 110

Pro Met Leu Gln Glu Ala Ile Arg Met Gly Phe Asp Phe Lys Asp Val
            115                 120                 125

Lys Lys Ile Met Glu Glu Arg Ile Gln Thr Ser Gly Ser Asn Tyr Lys
    130                 135                 140

Thr Leu Glu Val Leu Val Ala Asp Leu Val Ser Ala Gln Lys Asp Thr
145                 150                 155                 160

Thr Glu Asn Glu Leu Asn Gln Thr Ser Leu Gln Arg Glu Ile Ser Pro
                165                 170                 175

Glu Glu Pro Leu Arg Arg Leu Gln Glu Glu Lys Leu Cys Lys Ile Cys
            180                 185                 190

Met Asp Arg Tyr Ile Ala Val Val Phe Ile Pro Cys Gly His Leu Val
            195                 200                 205

Thr Cys Lys Gln Cys Ala Glu Ala Val Asp Arg Cys Pro Met Cys Ser
    210                 215                 220

Ala Val Ile Asp Phe Lys Gln Arg Val Phe Met Ser
225                 230                 235
```

<210> SEQ ID NO 3
<211> LENGTH: 1588
<212> TYPE: DNA
<213> ORGANISM: Homo sapiens

<400> SEQUENCE: 3

```
gaaaaggtgg acaagtccta ttttcaagag aagatgactt ttaacagttt tgaaggatct    60
aaaacttgtg tacctgcaga catcaataag gaagaagaat tgtagaaga gtttaataga   120
ttaaaaactt ttgctaattt tccaagtggt agtcctgttt cagcatcaac actggcacga   180
gcagggtttc tttatactgg tgaaggagat accgtgcggt gctttagttg tcatgcagct   240
gtagatagat ggcaatatgg agactcagca gttggaagac acaggaaagt atccccaaat   300
tgcagattta tcaacggctt ttatcttgaa aatagtgcca cgcagtctac aaattctggt   360
atccagaatg gtcagtacaa agttgaaaac tatctgggaa gcagagatca ttttgcctta   420
gacaggccat ctgagacaca tgcagactat cttttgagaa ctgggcaggt tgtagatata   480
tcagacacca tatacccgag gaaccctgcc atgtatagtg aagaagctag attaaagtcc   540
tttcagaact ggccagacta tgctcaccta accccaagag agttagcaag tgctggactc   600
tactacacag gtattggtga ccaagtgcag tgcttttgtt gtggtggaaa actgaaaaat   660
tgggaacctt gtgatcgtgc ctggtcagaa cacaggcgac actttcctaa ttgcttcttt   720
gttttgggcc ggaatcttaa tattcgaagt gaatctgatg ctgtgagttc tgataggaat   780
ttcccaaatt caacaaatct tccaagaaat ccatccatgg cagattatga agcacggatc   840
tttactttg gacatggat atactcagtt aacaaggagc agcttgcaag agctggattt   900
tatgctttag gtgaaggtga taaagtaaag tgctttcact gtggaggagg gctaactgat   960
tggaagccca gtgaagaccc ttgggaacaa catgctaaat ggtatccagg gtgcaaatat  1020
ctgttagaac agaagggaca agaatatata aacaatattc atttaactca ttcacttgag  1080
gagtgtctgg taagaactac tgagaaaaca ccatcactaa ctagaagaat tgatgatacc  1140
atcttccaaa atcctatggt acaagaagct atacgaatgg ggttcagttt caaggacatt  1200
```

-continued

```
aagaaaataa tggaggaaaa aattcagata tctgggagca actataaatc acttgaggtt      1260
ctggttgcag atctagtgaa tgctcagaaa gacagtatgc aagatgagtc aagtcagact      1320
tcattacaga aagagattag tactgaagag cagctaaggc gcctgcaaga ggagaagctt      1380
tgcaaaatct gtatggatag aaatattgct atcgttttg ttccttgtgg acatctagtc       1440
acttgtaaac aatgtgctga agcagttgac aagtgtccca tgtgctacac agtcattact      1500
ttcaagcaaa aaatttttat gtcttaatct aactctatag taggcatgtt atgttgttct      1560
tattaccctg attgaatgtg tgatgtga                                         1588
```

<210> SEQ ID NO 4
<211> LENGTH: 236
<212> TYPE: PRT
<213> ORGANISM: Homo sapiens

<400> SEQUENCE: 4

```
Met Ala Asp Tyr Glu Ala Arg Ile Phe Thr Phe Gly Thr Trp Ile Tyr
  1               5                  10                  15

Ser Val Asn Lys Glu Gln Leu Ala Arg Ala Gly Phe Tyr Ala Leu Gly
                 20                  25                  30

Glu Gly Asp Lys Val Lys Cys Phe His Cys Gly Gly Gly Leu Thr Asp
             35                  40                  45

Trp Lys Pro Ser Glu Asp Pro Trp Glu Gln His Ala Lys Trp Tyr Pro
         50                  55                  60

Gly Cys Lys Tyr Leu Leu Glu Gln Lys Gly Gln Glu Tyr Ile Asn Asn
 65                  70                  75                  80

Ile His Leu Thr His Ser Leu Glu Glu Cys Leu Val Arg Thr Thr Glu
                 85                  90                  95

Lys Thr Pro Ser Leu Thr Arg Arg Ile Asp Asp Thr Ile Phe Gln Asn
            100                 105                 110

Pro Met Val Gln Glu Ala Ile Arg Met Gly Phe Ser Phe Lys Asp Ile
        115                 120                 125

Lys Lys Ile Met Glu Glu Lys Ile Gln Ile Ser Gly Ser Asn Tyr Lys
    130                 135                 140

Ser Leu Glu Val Leu Val Ala Asp Leu Val Asn Ala Gln Lys Asp Ser
145                 150                 155                 160

Met Gln Asp Glu Ser Ser Gln Thr Ser Leu Gln Lys Glu Ile Ser Thr
                165                 170                 175

Glu Glu Gln Leu Arg Arg Leu Gln Glu Glu Lys Leu Cys Lys Ile Cys
            180                 185                 190

Met Asp Arg Asn Ile Ala Ile Val Phe Val Pro Cys Gly His Leu Val
        195                 200                 205

Thr Cys Lys Gln Cys Ala Glu Ala Val Asp Lys Cys Pro Met Cys Tyr
    210                 215                 220

Thr Val Ile Thr Phe Lys Gln Lys Ile Phe Met Ser
225                 230                 235
```

<210> SEQ ID NO 5
<211> LENGTH: 500
<212> TYPE: DNA
<213> ORGANISM: Homo sapiens
<220> FEATURE:
<221> NAME/KEY: misc_feature
<222> LOCATION: (1)...(500)
<223> OTHER INFORMATION: n = A,T,C or G

<400> SEQUENCE: 5

-continued

```
caactacaca cgtgtgtgtg cgcgtgtgta taaaacacag tgcactaata ctcagccttt      60
aaaaaaaatg ccacttgcaa caacgtagat ggagctggac gatatcatgc taaaattatg     120
caaagtgaaa caagcacaaa aaagaacgag acacgggcgt ggggcacgag gtgctcactg     180
ngcaagcgcc cactccaccg cgtggtttcc agctggaggc tgggagcgtt ngtggcttcc     240
tcttttcttg ctgacccttc ggagctctgg gaagtggctg caccttggcg gctcccagà     300 gcgcgcggtg ctaatcgtgg gtcgtcagcc tgggtggctg ggcccggctt agggcagggt     360
ttggcatttc caatggtagg gggctcggac cgtccctccg cgggaccctc ccgttgggac     420
aaggccgatc gcctgggcgg ttggagccgc tatcctggcg cgagacggtg gacaagtcct     480
atattcaaga gaagataact                                                  500
```

```
<210> SEQ ID NO 6
<211> LENGTH: 67
<212> TYPE: PRT
<213> ORGANISM: Artificial Sequence
<220> FEATURE:
<223> OTHER INFORMATION: Based on Cydia pomonella and Orgyia
      pseudotsugata
<221> NAME/KEY: VARIANT
<222> LOCATION: (1)...(67)
<223> OTHER INFORMATION: Xaa = Any Amino Acid
<221> NAME/KEY: VARIANT
<222> LOCATION: (1)...(67)
<223> OTHER INFORMATION: Xaa = Any Amino Acid

<400> SEQUENCE: 6

Xaa Xaa Xaa Arg Xaa Xaa Xaa Xaa Xaa Xaa Xaa Xaa Xaa Xaa Xaa
 1               5                  10                  15

Xaa Xaa Xaa Xaa Xaa Xaa Xaa Xaa Gly Xaa Xaa Xaa Xaa Xaa Xaa
            20                  25                  30

Xaa Xaa Xaa Xaa Cys Xaa Xaa Cys Xaa Xaa Xaa Xaa Xaa Xaa Xaa
        35                  40                  45

Xaa Xaa Xaa Xaa Xaa Xaa Xaa Xaa His Xaa Xaa Xaa Xaa Xaa Cys
    50                  55                  60

Xaa Xaa Xaa
65
```

```
<210> SEQ ID NO 7
<211> LENGTH: 68
<212> TYPE: PRT
<213> ORGANISM: Artificial Sequence
<220> FEATURE:
<223> OTHER INFORMATION: Based on Cydia pomonella and Orgyia
      pseudotsugata
<221> NAME/KEY: VARIANT
<222> LOCATION: (1)...(68)
<223> OTHER INFORMATION: Xaa = Any Amino Acid
<221> NAME/KEY: VARIANT
<222> LOCATION: (1)...(68)
<223> OTHER INFORMATION: Xaa = Any Amino Acid

<400> SEQUENCE: 7

Xaa Xaa Xaa Arg Xaa Xaa Xaa Xaa Xaa Xaa Xaa Xaa Xaa Xaa Xaa
 1               5                  10                  15

Xaa Xaa Xaa Xaa Xaa Xaa Xaa Xaa Gly Xaa Xaa Xaa Xaa Xaa Xaa
            20                  25                  30

Xaa Xaa Xaa Xaa Xaa Cys Xaa Xaa Cys Xaa Xaa Xaa Xaa Xaa Xaa
        35                  40                  45

Xaa Xaa Xaa Xaa Xaa Xaa Xaa Xaa Xaa His Xaa Xaa Xaa Xaa Xaa
    50                  55                  60
```

Cys Xaa Xaa Xaa
65

<210> SEQ ID NO 8
<211> LENGTH: 69
<212> TYPE: PRT
<213> ORGANISM: Artificial Sequence
<220> FEATURE:
<223> OTHER INFORMATION: Based on Cydia pomonella and Orgyia
      pseudotsugata
<221> NAME/KEY: VARIANT
<222> LOCATION: (1)...(69)
<223> OTHER INFORMATION: Xaa = Any Amino Acid
<221> NAME/KEY: VARIANT
<222> LOCATION: (1)...(69)
<223> OTHER INFORMATION: Xaa = Any Amino Acid

<400> SEQUENCE: 8

Xaa Xaa Xaa Arg Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Gly Xaa Xaa Xaa Xaa
             20                  25                  30

Xaa Xaa Xaa Xaa Xaa Xaa Cys Xaa Xaa Cys Xaa Xaa Xaa Xaa Xaa
         35                  40                  45

Xaa Xaa Xaa Xaa Xaa Xaa Xaa Xaa Xaa His Xaa Xaa Xaa Xaa Xaa
     50                  55                  60

Xaa Cys Xaa Xaa Xaa
65

<210> SEQ ID NO 9
<211> LENGTH: 70
<212> TYPE: PRT
<213> ORGANISM: Artificial Sequence
<220> FEATURE:
<223> OTHER INFORMATION: Based on Cydia pomonella and Orgyia
      pseudotsugata
<221> NAME/KEY: VARIANT
<222> LOCATION: (1)...(70)
<223> OTHER INFORMATION: Xaa = Any Amino Acid
<221> NAME/KEY: VARIANT
<222> LOCATION: (1)...(70)
<223> OTHER INFORMATION: Xaa = Any Amino Acid

<400> SEQUENCE: 9

Xaa Xaa Xaa Arg Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Gly Xaa Xaa Xaa Xaa
             20                  25                  30

Xaa Xaa Xaa Xaa Xaa Xaa Xaa Cys Xaa Xaa Cys Xaa Xaa Xaa Xaa Xaa
         35                  40                  45

Xaa Xaa Xaa Xaa Xaa Xaa Xaa Xaa Xaa Xaa His Xaa Xaa Xaa Xaa
     50                  55                  60

Xaa Xaa Cys Xaa Xaa Xaa
65                  70

<210> SEQ ID NO 10
<211> LENGTH: 35
<212> TYPE: PRT
<213> ORGANISM: Artificial Sequence
<220> FEATURE:
<223> OTHER INFORMATION: Based on Cydia pomonella and Orgyia
      pseudotsugata
<221> NAME/KEY: VARIANT
<222> LOCATION: (1)...(35)
<223> OTHER INFORMATION: Xaa = Any Amino Acid

```
<221> NAME/KEY: VARIANT
<222> LOCATION: (1)...(35)
<223> OTHER INFORMATION: Xaa = Any Amino Acid

<400> SEQUENCE: 10

Cys Xaa Xaa Cys Xaa Xaa Xaa Xaa Xaa Xaa Xaa Xaa Xaa Xaa Cys
1               5                   10                  15

Xaa His Xaa Xaa Xaa Cys Xaa Xaa Cys Xaa Xaa Xaa Xaa Xaa Cys
            20                  25                  30

Xaa Xaa Cys
        35
```